United States Patent
Oki et al.

(10) Patent No.: US 11,509,870 B2
(45) Date of Patent: Nov. 22, 2022

(54) IMAGE ACQUISITION SYSTEM AND IMAGE ACQUISITION METHOD

(71) Applicant: Sony Group Corporation, Tokyo (JP)

(72) Inventors: Tomoyuki Oki, Tokyo (JP); Satoshi Nagae, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 17/288,930

(22) PCT Filed: Oct. 23, 2019

(86) PCT No.: PCT/JP2019/041440
§ 371 (c)(1),
(2) Date: Apr. 27, 2021

(87) PCT Pub. No.: WO2020/095671
PCT Pub. Date: May 14, 2020

(65) Prior Publication Data
US 2021/0289176 A1 Sep. 16, 2021

(30) Foreign Application Priority Data
Nov. 7, 2018 (JP) .............................. JP2018-209429

(51) Int. Cl.
*H04N 9/097* (2006.01)
*H04N 5/225* (2006.01)
(Continued)

(52) U.S. Cl.
CPC ......... *H04N 9/097* (2013.01); *A61B 1/00009* (2013.01); *A61B 1/04* (2013.01);
(Continued)

(58) Field of Classification Search
CPC .. H04N 9/097; H04N 5/2256; H04N 5/23229; A61B 1/00009; A61B 1/04; A61B 1/0638
See application file for complete search history.

(56) References Cited

U.S. PATENT DOCUMENTS 8,890,946 B2 * 11/2014 Publicover ......... H04N 5/23219
348/78
9,609,230 B1 * 3/2017 Bakshi ............. H04N 5/232933
(Continued)

FOREIGN PATENT DOCUMENTS

| CN | 104523214 A | 4/2015 |
|---|---|---|
| JP | 2011-127933 A | 6/2011 |
| JP | 2018-27272 A | 2/2018 |

OTHER PUBLICATIONS

International Search Report and Written Opinion dated Dec. 24, 2019, received for PCT Application PCT/JP2019/041440, Filed on Oct. 23, 2019, 11 pages including English Translation.

*Primary Examiner* — Zaihan Jiang
(74) *Attorney, Agent, or Firm* — Xsensus LLP

(57) ABSTRACT

An image acquisition system includes: a first narrowband light source that emits first narrowband light for exciting a luminescent agent that exists in an observation target and emits light having a wavelength belonging to a visible light wavelength band; a second narrowband light source that emits second narrowband light in a wavelength band of ±30 nm of a peak light emission wavelength of the luminescent agent; a broadband light source that emits broadband light for illuminating the observation target; a first image sensor on which an image of light in a light emission wavelength band including a wavelength corresponding to light emitted from the luminescent agent is formed; and a second image sensor including one or more image sensors on which an image of light in a wavelength band other than the light emission wavelength band is formed.

16 Claims, 14 Drawing Sheets

(51) Int. Cl.
  *H04N 5/232*   (2006.01)
  *A61B 1/06*    (2006.01)
  *A61B 1/00*    (2006.01)
  *A61B 1/04*    (2006.01)
  *A61B 90/20*   (2016.01)

(52) U.S. Cl.
  CPC ......... *A61B 1/0638* (2013.01); *H04N 5/2256* (2013.01); *H04N 5/23229* (2013.01); *A61B 90/20* (2016.02); *H04N 2005/2255* (2013.01)

(56) References Cited

U.S. PATENT DOCUMENTS

| | | | |
|---|---|---|---|
| 9,699,377 B2 * | 7/2017 | You | H04N 5/2256 |
| 2009/0117331 A1 * | 5/2009 | Fung | D21H 27/40 |
| | | | 428/154 |
| 2010/0297286 A1 * | 11/2010 | Boatman | B31F 1/07 |
| | | | 425/517 |
| 2010/0297402 A1 * | 11/2010 | Boatman | D21H 27/02 |
| | | | 428/174 |
| 2014/0012400 A1 * | 1/2014 | Hidaka | F21V 23/0478 |
| | | | 700/28 |
| 2016/0088241 A1 * | 3/2016 | Sung | G06V 40/19 |
| | | | 382/117 |
| 2016/0277660 A1 * | 9/2016 | Kaiser | G03B 15/06 |
| 2018/0052107 A1 | 2/2018 | Kim et al. | |
| 2018/0307123 A1 * | 10/2018 | Kaiser | G03B 15/06 |
| 2019/0170647 A1 * | 6/2019 | Ikenaga | G01N 21/6458 |
| 2019/0356837 A1 * | 11/2019 | Bakshi | H04N 9/12 |

\* cited by examiner

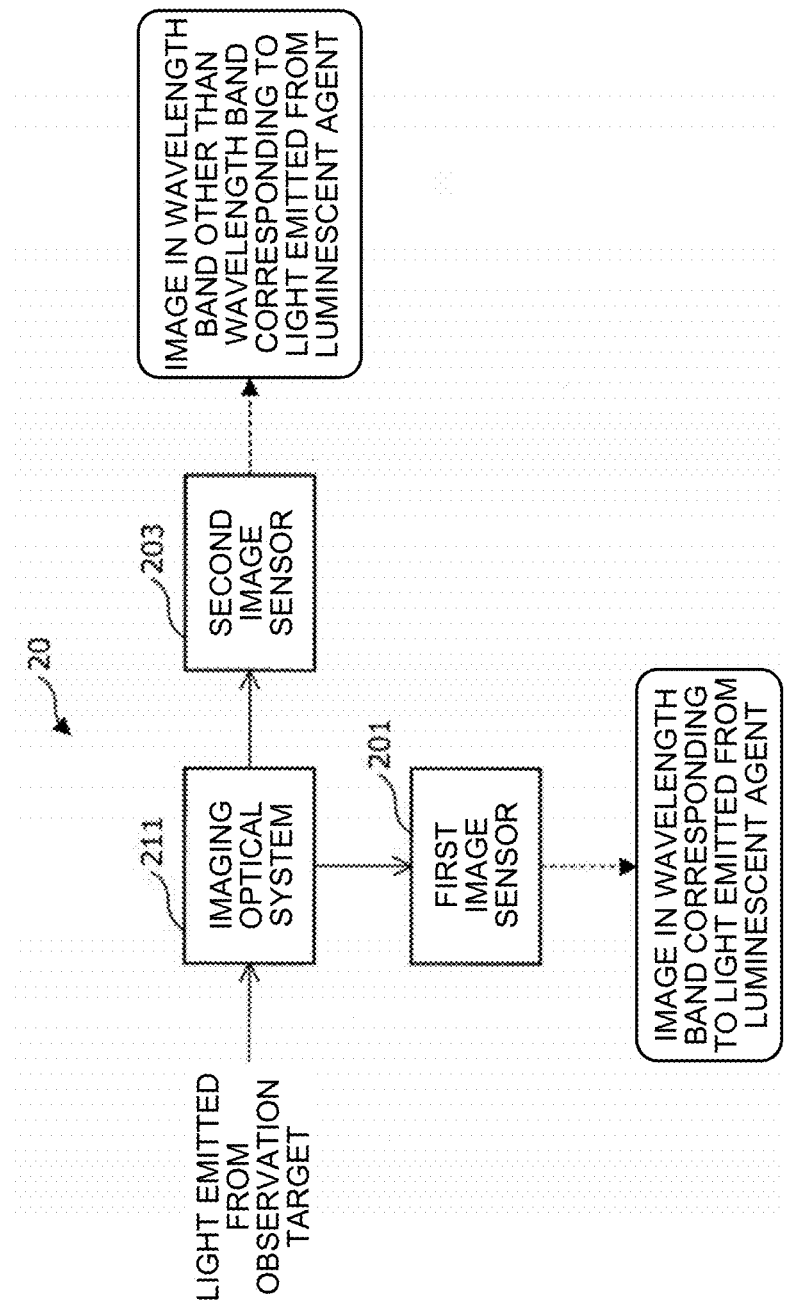

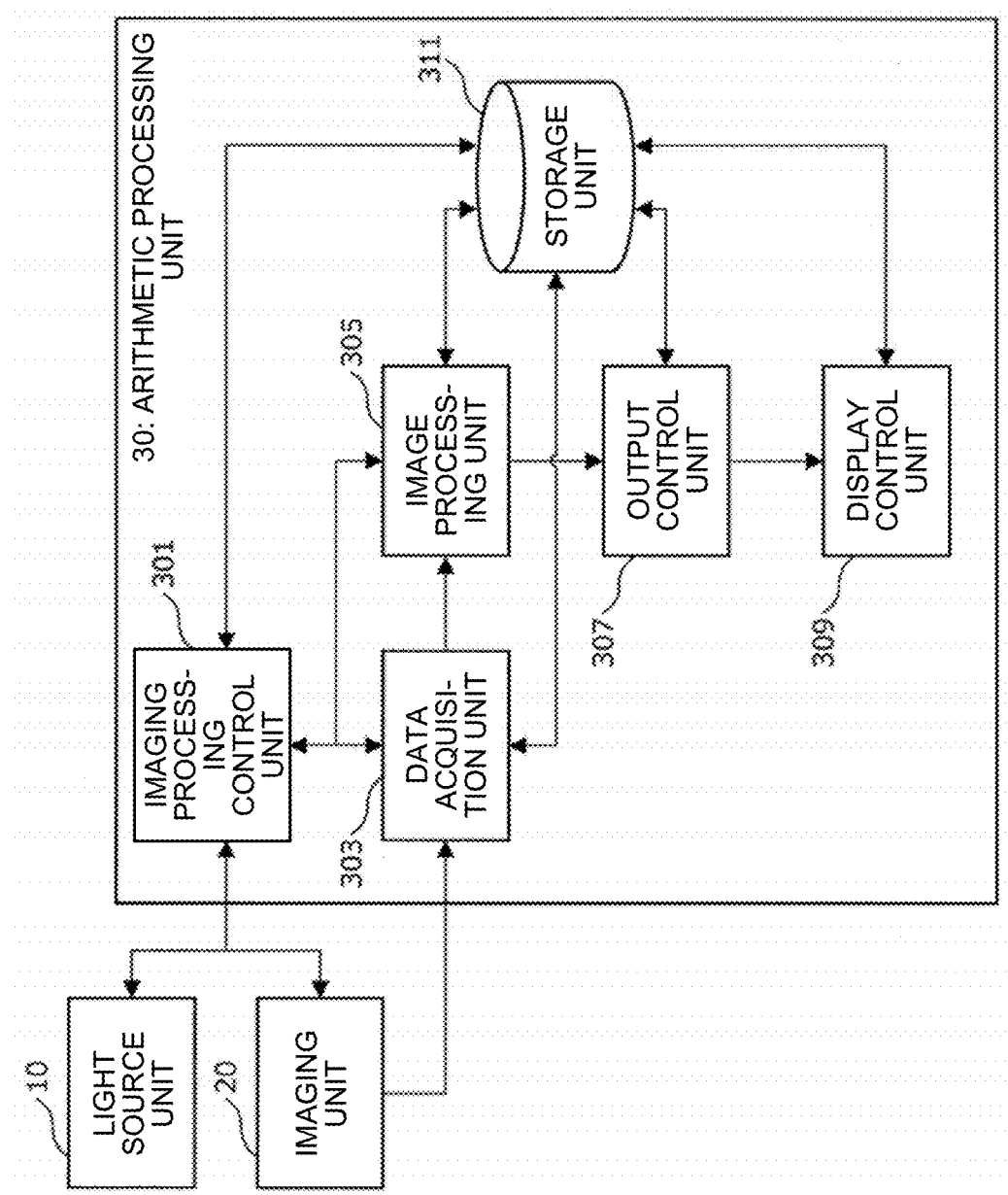

IMAGE ACQUISITION SYSTEM AND IMAGE ACQUISITION METHOD

CROSS-REFERENCE TO RELATED APPLICATIONS

The present application is based on PCT filing PCT/JP2019/041440, filed Oct. 23, 2019, which claims priority to JP 2018-209429, filed Nov. 7, 2018, the entire contents of each are incorporated herein by reference.

FIELD

The present disclosure relates to an image acquisition system and an image acquisition method.

BACKGROUND

In recent years, a technology, in which a patient to which an agent is administered is irradiated with excitation light with which the agent reacts, and light (for example, fluorescence) emitted from the agent is observed to support surgical operations or diagnosis by doctors, has received attentions. Here, since the light emitted from the agent is very weak, it is usual to turn off a general illumination used for surgery or the like, use only the excitation light, and observe the light from the agent. However, in such a case, since only an image in which only the light emitted from the agent shines can be obtained, it is difficult for the doctor to perform some surgical operations while observing the light emitted from the agent.

Therefore, for example, Patent Literature 1 proposes a technology in which two or more image sensors for capturing an image of light from an observation target are prepared, and the light from the observation target is separated, such that a normal image obtained by using a general illumination and a luminescence image obtained by capturing an image of the light emitted from an agent are obtained by using different image sensors, respectively. For example, it is possible to perform demultiplexing of a background image and a fluorescence image with a fluorescence wavelength by using an agent which fluoresces and is excited with light (more specifically, near-infrared light) other than light in a visible light wavelength band, such as a fluorescent agent called indocyanine green (ICG), and further using the above-described technology. As a result, it becomes possible to acquire the background image and the fluorescence image at the same time, and the doctor can perform an appropriate surgical operation or make a diagnosis on a portion characterized by the fluorescence image while viewing the background image.

CITATION LIST

Patent Literature

Patent Literature 1: JP 2018-27272 A

SUMMARY

Technical Problem

However, even when using the above-described technology in which light from an observation target is separated, in a case where a wavelength of light emitted from a luminescent agent belongs to the visible light wavelength band, the image sensor receives light in which illumination light and the light emitted from the luminescent agent are mixed. As a result, a signal-to-noise ratio (S/N ratio) may decrease in a luminescence image such as a fluorescence image. Therefore, there is still room for improvement in technology capable of acquiring a luminescence image without causing a decrease in the signal-to-noise ratio of the luminescence image even in a case where a wavelength of light emitted from a luminescent agent belongs to the visible light wavelength band.

Therefore, in view of the above circumstances, the present disclosure proposes an image acquisition system and an image acquisition method that are capable of acquiring a luminescence image without causing a decrease in a signal-to-noise ratio of the luminescence image even in a case where a wavelength of light emitted from a luminescent agent belongs to the visible light wavelength band.

Solution to Problem

According to the present disclosure, an image acquisition system, comprising: a first narrowband light source that emits first narrowband light for exciting a luminescent agent that exists in an observation target and emits light having a wavelength belonging to a visible light wavelength band; a second narrowband light source that emits second narrowband light in a wavelength band of ±30 nm of a peak light emission wavelength of the luminescent agent; a broadband light source that emits broadband light for illuminating the observation target, the broadband light being in a wavelength band broader than those of the first narrowband light and the second narrowband light; a first image sensor on which an image of light in a light emission wavelength band including a wavelength corresponding to light emitted from the luminescent agent is formed; and a second image sensor including one or more image sensors on which an image of light in a wavelength band other than the light emission wavelength band is formed, wherein a first captured image obtained from the first image sensor and a second captured image obtained from the second image sensor are combined with each other to obtain a captured image related to the observation target, is provided.

Furthermore, according to the present disclosure, an image acquisition method, comprising: irradiating an observation target with illumination light from at least one of a first narrowband light source that emits first narrowband light for exciting a luminescent agent that exists in the observation target and emits light having a wavelength belonging to a visible light wavelength band or a second narrowband light source that emits second narrowband light in a wavelength band of ±30 nm of a peak light emission wavelength of the luminescent agent, and a broadband light source that emits broadband light for illuminating the observation target, the broadband light being in a wavelength band broader than those of the first narrowband light and the second narrowband light; receiving, by each of a first image sensor on which an image of light in a light emission wavelength band including a wavelength corresponding to light emitted from the luminescent agent is formed and a second image sensor including one or more image sensors on which an image of light in a wavelength band other than the light emission wavelength band is formed, light from the observation target; and combining a first captured image obtained from the first image sensor and a second captured image obtained from the second image sensor with each other to obtain a captured image related to the observation target, is provided.

According to the present disclosure, an observation target is irradiated with at least one of first narrowband light or second narrowband light, and broadband light as illumination light, an image of light from the observation target is formed on the first image sensor and the second image sensor, and the first captured image and the second captured image are combined with each other to obtain a captured image related to the observation target.

BRIEF DESCRIPTION OF DRAWINGS

FIG. 8 is an explanatory diagram schematically illustrating an example of the configuration of the imaging unit in the image acquisition system according to the embodiment.

FIG. 11 is a block diagram illustrating an example of a configuration of an arithmetic processing unit in the image acquisition system according to the embodiment.

DESCRIPTION OF EMBODIMENTS

Figure 1:
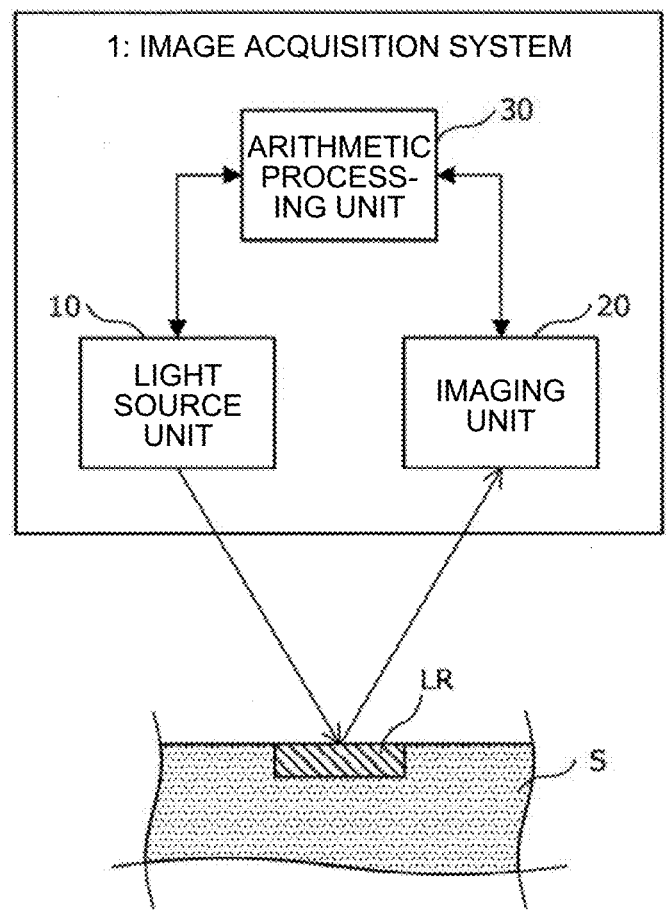
FIG. 1 is an explanatory diagram schematically illustrating an overall configuration of an image acquisition system according to an embodiment of the present disclosure.

Hereinafter, preferred embodiments of the present disclosure will be described in detail with reference to the accompanying drawings. In the present specification and the drawings, components having substantially the same functional configuration will be denoted by the same reference numerals to omit an overlapping description.

Note that the description will be provided in the following order.

1. Examination Conducted by Present Inventors
2. Embodiment
2.1 Overall Configuration of Image Acquisition System
2.2 Configurations Of Light Source Unit and Imaging Unit in Image Acquisition System
2.3 Example of Detailed Configuration of Light Source Unit
2.4 Example of Detailed Configuration of Imaging Unit
2.5 Example of Configuration of Arithmetic Processing Unit
2.6 Example of Hardware Configuration of Arithmetic Processing Unit
2.7 Image Acquisition Method
2.8 Conclusion
3. Examples (Examination Conducted by Present Inventors)

Prior to describing an image acquisition system and an image acquisition method according to an embodiment of the present disclosure, the contents of examination conducted by the present inventors to implement a technology capable of acquiring a luminescence image without causing a decrease in a signal-to-noise ratio of the luminescence image will be briefly described below.

As described above, the technology, in which a patient to which an agent is administered is illuminated with excitation light with which the agent reacts, and light (for example, fluorescence) emitted from the agent is observed to support surgical operations or diagnosis by doctors, has received attentions. For example, a luminescent agent called 5-aminolevulinic acid (5-ALA) is only taken up by and deposited in tumor cells, and is metabolized to protoporphyrin IX (PPIX) which is a fluorescent substance. The PPIX fluoresces in red (640 nm) when exposed to bluish-violet (405 nm) light, which is useful for intraoperative determination in brain surgery. In recent years, a surgical microscope used in brain surgery, ophthalmology, cardiac surgery, and the like often has the fluorescence observation function as described above, and a surgical endoscope such as a rigid endoscope or a flexible endoscope having the fluorescence observation function has been developed.

Conventionally, in the surgical microscope or surgical endoscope, various lamp light sources such as a xenon lamp and a halogen lamp, and a single light source such as a white LED light source have been mainly used as an illumination light source. Therefore, for example, in order to add the fluorescence observation function, it is required to extract excitation light for generating fluorescence from a single light source with an optical filter or the like, or to newly multiplex the excitation light. Further, since fluorescence from the luminescent agent is very weak light, it is usual to turn off a general illumination such as an astral lamp and use only the excitation light for fluorescence observation. In such a case, since an image in which only the fluorescence shines is acquired, it is possible to observe a portion of interest, but it is difficult to perform a surgical operation because the background becomes dark.

The following two approaches can be considered as solutions for doctors and the like to perform a surgical operation while observing light (for example, fluorescence) emitted from a portion of interest. The first approach is a method of acquiring an image in a time-division manner, and the second approach is a method of separating light (luminous flux) from a portion of interest.

In the time division method, which is the first approach, normal light used for normal observation (observation of a portion of interest using normal visible light, for example, under an astral lamp) and excitation light are alternately radiated rapidly on a time axis. Then, a normal observation image captured by using the normal light and a fluorescence observation image obtained by capturing fluorescence generated from a luminescent agent by the excitation light are alternately captured. Thereafter, a composite image is obtained by combining the obtained normal observation image and fluorescence observation image, and the obtained composite image is displayed.

However, in the time division method as described above, since the shutter speed in an imaging device such as a camera is linked with the emission of normal light or excitation light from a light source, blinking of light occurs, and a user such as a doctor suffers from stress. In order to prevent such blinking of light, it is necessary to blink the light at a high speed at which the user is not bothered by the blinking, and to synchronize the high-speed blinking of the light with the shutter of the imaging device, which is technically difficult.

Further, in such a time division method, since the normal observation image and the fluorescence observation image are alternately captured, the frame rate decreases. When the frame rate decreases, it becomes difficult to follow a movement of an observation target in a case where such a movement is rapid, which may hinder quick response in a surgical operation such as hemostasis.

On the other hand, in the luminous flux separation method, which is the second approach, two or more image sensors are prepared, and one of the image sensors is a dedicated element for capturing an image of fluorescence from a luminescent agent. In this case, as mentioned earlier, in a case where the luminescent agent is an agent that fluoresces and is excited with light (more specifically, near-infrared light) other than light in the visible light wavelength band, such as ICG, simultaneous observation becomes possible by demultiplexing the normal observation image, which is the background image, and the fluorescence observation image with a fluorescence wavelength.

However, even when using the above-described luminous flux separation method, in a case where a wavelength of light emitted from a luminescent agent belongs to the visible light wavelength band, the image sensor receives light in which illumination light and the light emitted from the luminescent agent are mixed. As a result, a signal-to-noise ratio (S/N ratio) may decrease in a luminescence image such as a fluorescence image.

As described above, under this circumstance, there is still room for improvement in technology capable of acquiring a luminescence image without causing a decrease in the signal-to-noise ratio of the luminescence image even in a case where a wavelength of light emitted from a luminescent agent belongs to the visible light wavelength band.

In order to overcome this circumstance, the present inventors have conducted diligent studies, and as a result, have implemented the present technology as described in detail below on the basis of the idea that a luminescence image can be acquired by using the luminous flux separation method without causing a decrease in the signal-to-noise ratio of the luminescence image even in a case where a wavelength emitted from a luminescent agent belongs to the visible light wavelength band, by using a specific light source and a specific imaging device and appropriately controlling the operating states of the light source and the imaging device.

Since the present technology as described in detail below adopts the luminous flux separation method, the above phenomenon that occurs in a case of adopting the time division method does not occur, and it is possible to improve the convenience of the doctor who is the user. Further, in the present technology as described in detail below, although the luminous flux separation method is adopted, it is possible to separate light emitted from a luminescent agent by controlling the light source and using a specific imaging optical system. As a result, it is possible to acquire a luminescence image without causing a decrease in the signal-to-noise ratio of the luminescence image even in a case where a wavelength of the light emitted from the luminescent agent belongs to the visible light wavelength band.

Hereinafter, the image acquisition system and the image acquisition method according to the embodiment of the present disclosure, which are implemented on the basis of the above idea, will be described in detail.

Embodiment

<Overall Configuration of Image Acquisition System>

In the following, first, an overall configuration of the image acquisition system according to the embodiment of the present disclosure will be briefly described with reference to FIG. 1. FIG. 1 is an explanatory diagram schematically illustrating the overall configuration of the image acquisition system according to the present embodiment.

In an image acquisition system 1 according to the present embodiment, a sample into which a luminescent agent (for example, various fluorescent reagents or phosphorescent reagents) LR that emits light having a wavelength belonging to the visible light wavelength band is introduced in advance is an observation target S, and a captured image of the observation target S is acquired by capturing an image of the observation target S.

Here, the observation target S to be observed by the image acquisition system 1 according to the present embodiment is not particularly limited, and various known samples into which various luminescent agents can be introduced can be the observation target. Examples of such an observation target S include various living tissues represented by organs of living organisms such as humans.

Further, the luminescent reagent LR previously introduced into the observation target S is not particularly limited, and various known luminescent reagents can be used as long as they contain a substance that emits light having a wavelength belonging to the visible light wavelength band. For example, examples of the fluorescent reagent that emits fluorescence having a wavelength belonging to the visible light wavelength band include fluorescein, 5-aminolevulinic acid (5-ALA), and Laserphyrin. It is assumed that at least one of the above-described luminescent reagents is introduced in advance into the observation target S focused on in the present embodiment.

The image acquisition system 1 that acquires the captured image of the observation target S as described above includes a light source unit 10, an imaging unit 20, and an arithmetic processing unit 30, as schematically illustrated in FIG. 1.

The light source unit 10 is a unit that irradiates the observation target S with predetermined illumination light under the control of the arithmetic processing unit 30. The imaging unit 20 is a unit that captures an image of a portion of the observation target S irradiated with the illumination light from the light source unit 10 and generates a plurality of predetermined types of captured images under the control of the arithmetic processing unit 30. The arithmetic processing unit 30 is a unit that controls the operating states of the light source unit 10 and the imaging unit 20, and generates a captured image of the observation target S that is focused on, by using the plurality of types of captured images obtained from the imaging unit 20.

Hereinafter, each of the light source unit 10, the imaging unit 20, and the arithmetic processing unit 30 included in the image acquisition system 1 according to the present embodiment will be described in detail.

<Configurations Of Light Source Unit and Imaging Unit>

Figure 2:
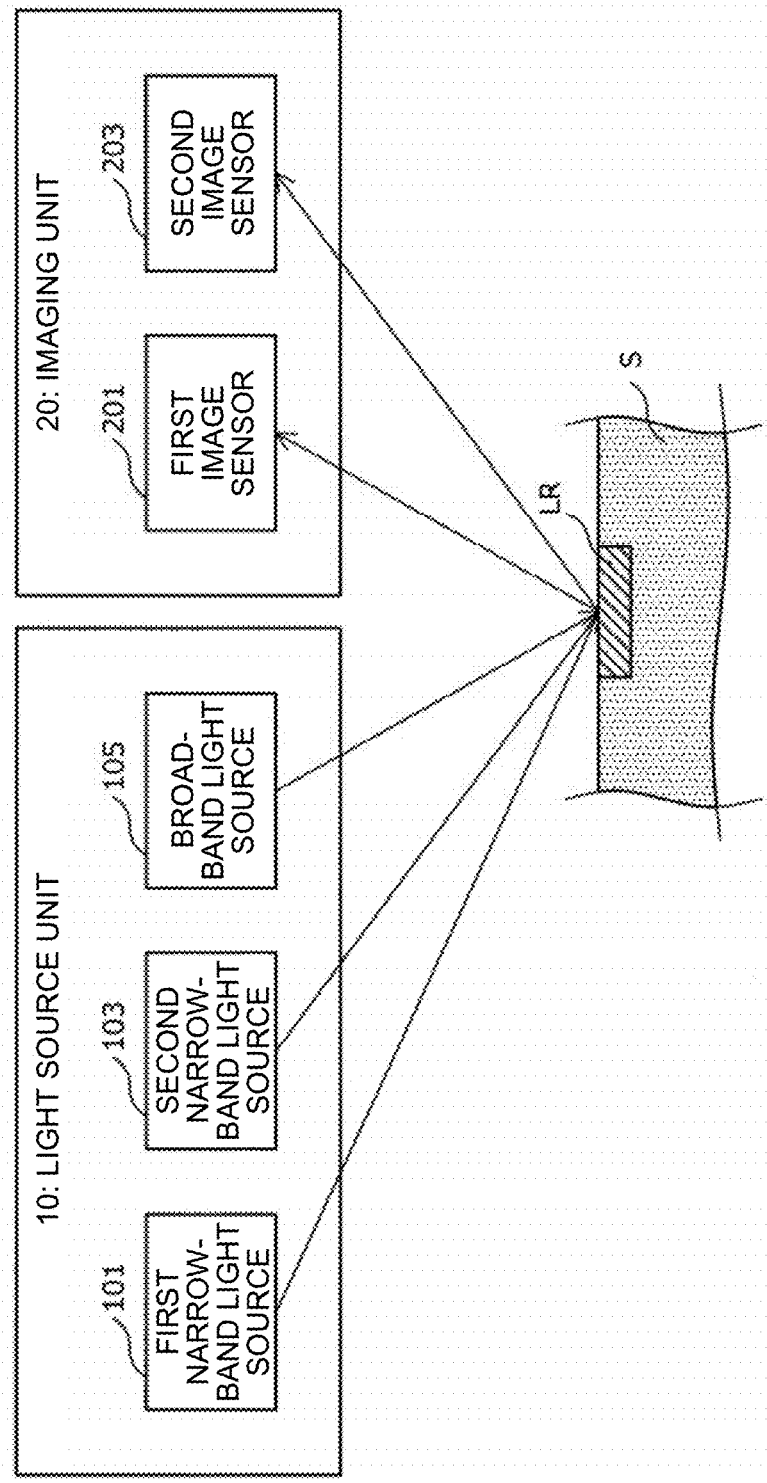
FIG. 2 is an explanatory diagram schematically illustrating configurations of a light source unit and an imaging unit in the image acquisition system according to the embodiment.

Next, the configurations of the light source unit 10 and the imaging unit 20 according to the present embodiment will be described with reference to FIG. 2. FIG. 2 is an explanatory diagram schematically illustrating the configurations of the light source unit and the imaging unit in the image acquisition system according to the present embodiment.

The light source unit 10 according to the present embodiment includes a first narrowband light source 101, a second narrowband light source 103, and a broadband light source 105, as schematically illustrated in FIG. 2.

The first narrowband light source 101 emits first narrowband light for exciting the luminescent agent LR existing in the observation target S, and the second narrowband light source 103 emits second narrowband light in a wavelength band of ±30 nm of a peak light emission wavelength of the luminescent agent LR. Further, the broadband light source 105 emits broadband light for illuminating the observation target, the broadband light being in a wavelength band broader than that of the first narrowband light and the second narrowband light.

Further, the imaging unit 20 according to the present embodiment includes a first image sensor 201 and a second image sensor 203, as schematically illustrated in FIG. 2.

An image of light in a light emission wavelength band including a wavelength corresponding to light emitted from the luminescent agent LR is formed on the first image sensor 201, and a captured image (first captured image) obtained by capturing the light in the light emission wavelength band is generated. Further, the second image sensor 203 includes one or more image sensors. An image of light in a wavelength band other than the above-described light emission wavelength band is formed on the second image sensor 203, and a captured image (second captured image) obtained by capturing the light in the wavelength band is generated.

In the image acquisition system 1 according to the present embodiment, the first captured image obtained from the first image sensor 201 and the second captured image obtained from the second image sensor 203 are combined with each other to obtain a captured image related to the observation target S.

As described above, in the image acquisition system 1 according to the present embodiment, a specific light source in which a narrowband light source and a broadband light source that satisfy specific conditions are combined is used, and the first image sensor on which an image of light in the light emission wavelength band is formed, and the second image sensor on which an image of light in a wavelength band other than the light emission wavelength band is formed are provided. As a result, the image acquisition system 1 according to the present embodiment can acquire a luminescence image without causing a decrease in the signal-to-noise ratio of the luminescence image even in a case where a wavelength of the light emitted from the luminescent agent LR belongs to the visible light wavelength band.

That is, in the image acquisition system 1 according to the present embodiment, both the first image sensor 201 and the second image sensor 203 are operated together at one imaging timing, and a captured image is generated in each image sensor. Here, in the image acquisition system 1 according to the present embodiment, an image of light in the light emission wavelength band including a wavelength corresponding to light (for example, fluorescence or phosphorescence) emitted from the luminescent agent LR that is focused on is formed on the first image sensor 201, and an image of light having a wavelength belonging to other wavelength bands is formed on the second image sensor 203. Further, in the image acquisition system 1 according to the present embodiment, the second narrowband light source 103 is set to emit the second narrowband light in the wavelength band of ±30 nm of the peak light emission wavelength of the luminescent agent LR that is focused on.

In a case of performing normal observation using visible light instead of the light emitted from the luminescent agent LR for the observation target S that is focused on, an image of the light (in other words, the second narrowband light) in the light emission wavelength band is formed on the first image sensor 201, and an image of the light (for example, the broadband light having a wavelength different from that of the second narrowband light) having a wavelength in a wavelength band other than the light emission wavelength band is formed on the second image sensor 203. Therefore, interpolation of light in the wavelength band missing in each captured image can be made by combining the first captured image obtained from the first image sensor 201 and the second captured image obtained from the second image sensor 203, and as a result, it is possible to obtain a color captured image similar to that in a case of performing the normal observation (observation of a portion of interest with normal visible light, for example, under an astral lamp).

Further, in a case of observing the light emitted from the luminescent agent LR for the observation target S that is focused on, an image of the light emitted from the luminescent agent LR is formed on the first image sensor 201 and an image of the light (that is, light having a wavelength other than that of the light emitted from the luminescent agent LR) having a wavelength in a wavelength band other than the light emission wavelength band is formed on the second image sensor 203. In the first captured image obtained from the first image sensor 201, only an image of the light emitted from the luminescent agent LR is formed, and thus the signal-to-noise ratio (S/N ratio) of the first captured image does not decrease. Further, by combining the first captured image obtained from the first image sensor 201 and the second captured image obtained from the second image sensor 203, it is possible to obtain a color captured image of the observation target S, in which the light emitted from the luminescent agent LR is superimposed.

As a result, the image acquisition system 1 according to the present embodiment can acquire a luminescence image without causing a decrease in the signal-to-noise ratio of the luminescence image even in a case where a wavelength of the light emitted from the luminescent agent LR belongs to the visible light wavelength band.

Note that the second narrowband light source 103 emits, preferably, the second narrowband light in a wavelength band of ±10 nm of the peak light emission wavelength of the luminescent agent LR that is focused on, and more preferably, the second narrowband light in a wavelength band of ±5 nm of the peak light emission wavelength. By using the second narrowband light source 103 that emits such a second narrowband light, it is possible to more surely acquire a luminescence image without causing a decrease in the signal-to-noise ratio of the luminescence image even in a case where a wavelength of the light emitted from the luminescent agent LR belongs to the visible light wavelength band.

<Example of Detailed Configuration of Light Source Unit 10>

Here, the narrowband light source used as the first narrowband light source 101 and the second narrowband light source 103 is not particularly limited, and various known narrowband light sources may be used as the first narrowband light source 101 and the second narrowband light source 103, independently of each other. Examples of such a narrowband light source include various laser light sources, semiconductor laser light sources, light emitting diodes, and the like. By using such a narrowband light source, the first narrowband light source 101 or the second narrowband light source 103 according to the present embodiment can be implemented more easily.

Further, the broadband light source used as the broadband light source 105 is not particularly limited, and various known broadband light sources can be used. As such a broadband light source, for example, various lamp light sources, light emitting diodes, and fluorescent material excitation light sources can be used. By using such a broadband light source, the broadband light source 105 according to the present embodiment can be implemented more easily, and for example, broadband white light can be easily implemented.

In the image acquisition system 1 according to the present embodiment, it is preferable that light having a predetermined color temperature and color coordinates is used as the illumination light for illuminating the observation target S, the light being obtained by at least multiplexing at least one of the first narrowband light or the second narrowband light described above, and the broadband light described above. By using the light having a predetermined color temperature and color coordinates as the illumination light, it is possible to more easily obtain a normal color captured image related to the observation target S or a color captured image of the observation target S in which the light emitted from the luminescent agent LR is superimposed.

Further, in the image acquisition system 1 according to the present embodiment, it is more preferable that the illumination light as described above is white light. By using white light as the illumination light, it is possible to more easily obtain a color captured image that is similar to that for observation of a portion of interest with normal visible light, for example, under an astral lamp.

Here, it is more preferable that the light having a predetermined color temperature and color coordinates, which is obtained by at least multiplexing at least one of the first narrowband light or the second narrowband light described above and the broadband light described above, is white light having a color temperature and color coordinates as described below. That is, it is more preferable that the light is white light obtained by multiplexing narrowband light and broadband light so that a color temperature is within a range of 5000 K or more and 6500 K or less, and color coordinates (X, Y) are within a range in which X: 0.3 or more and 0.4 or less and Y: 0.3 or more and 0.4 or less. When the color temperature and the color coordinates are within the above-described ranges, it is possible to implement better white light, and it is possible to more easily obtain a better color captured image.

In the image acquisition system 1 according to the present embodiment, it is preferable that the first narrowband light source 101, the second narrowband light source 103, and the broadband light source 105 as described above are driven independently of each other to control the intensity. By driving the first narrowband light source 101, the second narrowband light source 103, and the broadband light source 105 independently of each other, it is possible to more easily implement the illumination light having the color temperature and color coordinates as described above.

Further, it is preferable that, in the image acquisition system 1 according to the present embodiment, at least a blue narrowband light source that emits blue light, a green narrowband light source that emits green light, and a red narrowband light source that emits red light are included as the narrowband light sources, and at least one of the blue narrowband light source, the green narrowband light source, or the red narrowband light source is configured to function as the first narrowband light source 101 and/or the second narrowband light source 103 described above. When the image acquisition system 1 according to the present embodiment at least includes the blue narrowband light source, the green narrowband light source, and the red narrowband light source as described above, it is possible to more easily implement the white light having the color temperature and color coordinates as described above. Furthermore, it is possible to increase the number of feasible combinations of a color temperature and color coordinates in addition to the white light having the color temperature and color coordinates as described above.

In the light source unit 10 using the light source as described above, in a case of not observing the light emitted from the luminescent agent LR, it is preferable that light having the predetermined color temperature and color coordinates as described above is used as the illumination light, the light being implemented by multiplexing at least one of the first narrowband light or the second narrowband light and the broadband light. Further, in the light source unit 10 using the light source as described above, in a case of observing the light emitted from the luminescent agent LR, it is preferable that light having a predetermined color temperature and color coordinates is used as the illumination light, the light being implemented by suppressing the intensity of the second narrowband light and increasing or decreasing the intensities of the first narrowband light and the broadband light.

The intensity of the light emitted from the luminescent agent LR, whether fluorescence or phosphorescence, is extremely weak as compared with the intensity of the narrowband light emitted from the narrowband light source. Therefore, in a case of observing the light emitted from the luminescent agent LR, it is preferable to suppress the intensity of the second narrowband light as described above. As a result, it is possible to more surely form an image of the light emitted from the luminescent agent LR on the first image sensor 201. Further, when observing the light emitted from the luminescent agent LR, it is preferable that the light having the predetermined color temperature and color coordinates as described above is implemented by increasing or decreasing the intensities of the first narrowband light and the broadband light. By doing so, it is possible to obtain a color captured image (background image) that is similar to that for observation of a portion of interest with normal visible light, for example, under an astral lamp.

Note that in a case of observing the light emitted from the luminescent agent LR, it is preferable that the second narrowband light source 103 is turned off or controlled so that the drive voltage is lower than an oscillation threshold voltage of the second narrowband light. As a result, it is possible to more surely suppress the intensity of the second narrowband light, and more surely form an image of the light emitted from the luminescent agent LR on the first image sensor 201. In addition to the control as described above, for example, the drive voltage of the second narrowband light source 103 may be controlled so that the intensity of the second narrowband light is 1/100 or less of the intensity of the light emitted from the luminescent agent LR.

[Specific Example of Light Source Unit 10]

In the following, the light source unit 10 in the image acquisition system 1 according to the present embodiment in a case where, for example, 5-ALA is used as the luminescent agent LR, will be described in more detail with reference to FIGS. 3 to 7. By using the light source unit 10 as described below, even in a case of observing light (fluorescence) emitted from 5-ALA, it is possible to easily obtain an image in which a background image and a fluorescence image are superimposed in a state where the signal-to-noise ratio (S/N ratio) is high.

Figure 3:
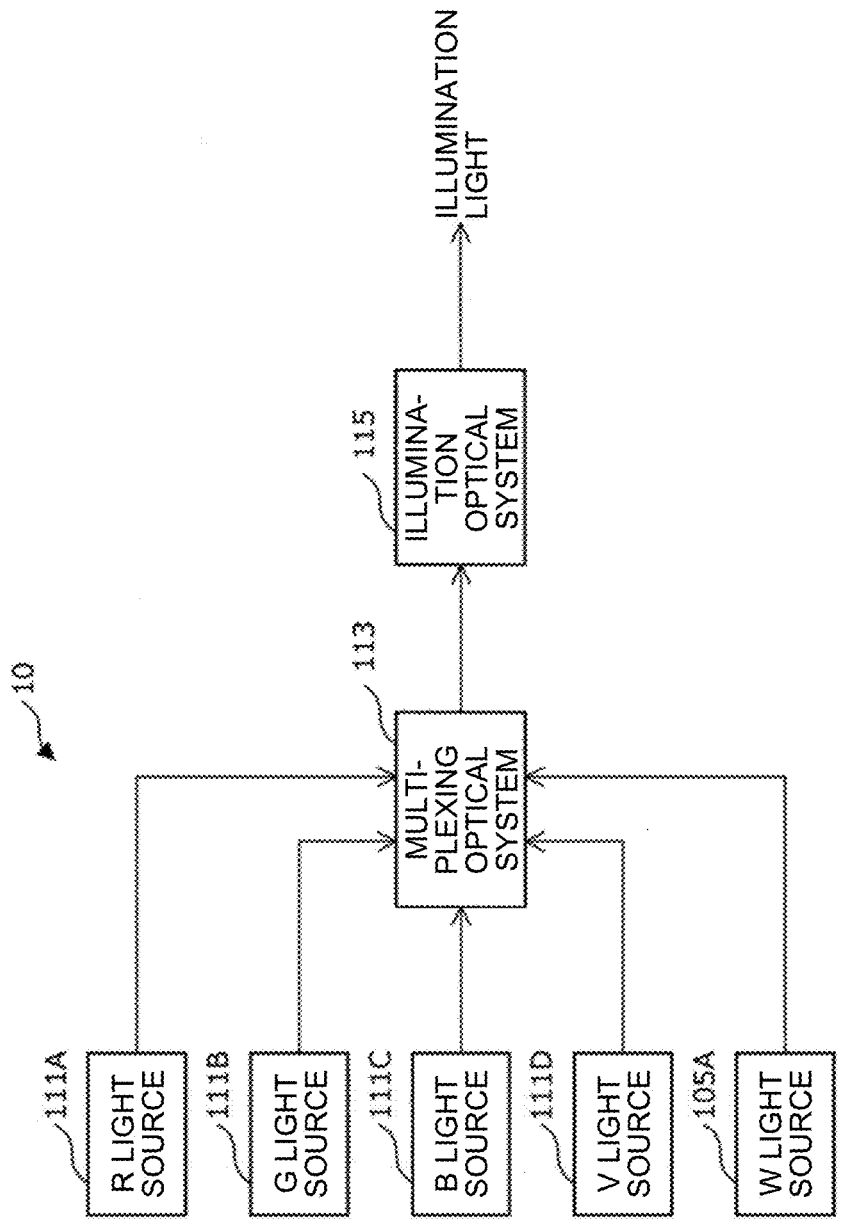
FIG. 3 is an explanatory diagram schematically illustrating an example of the configuration of the light source unit in the image acquisition system according to the embodiment.
Figure 4:
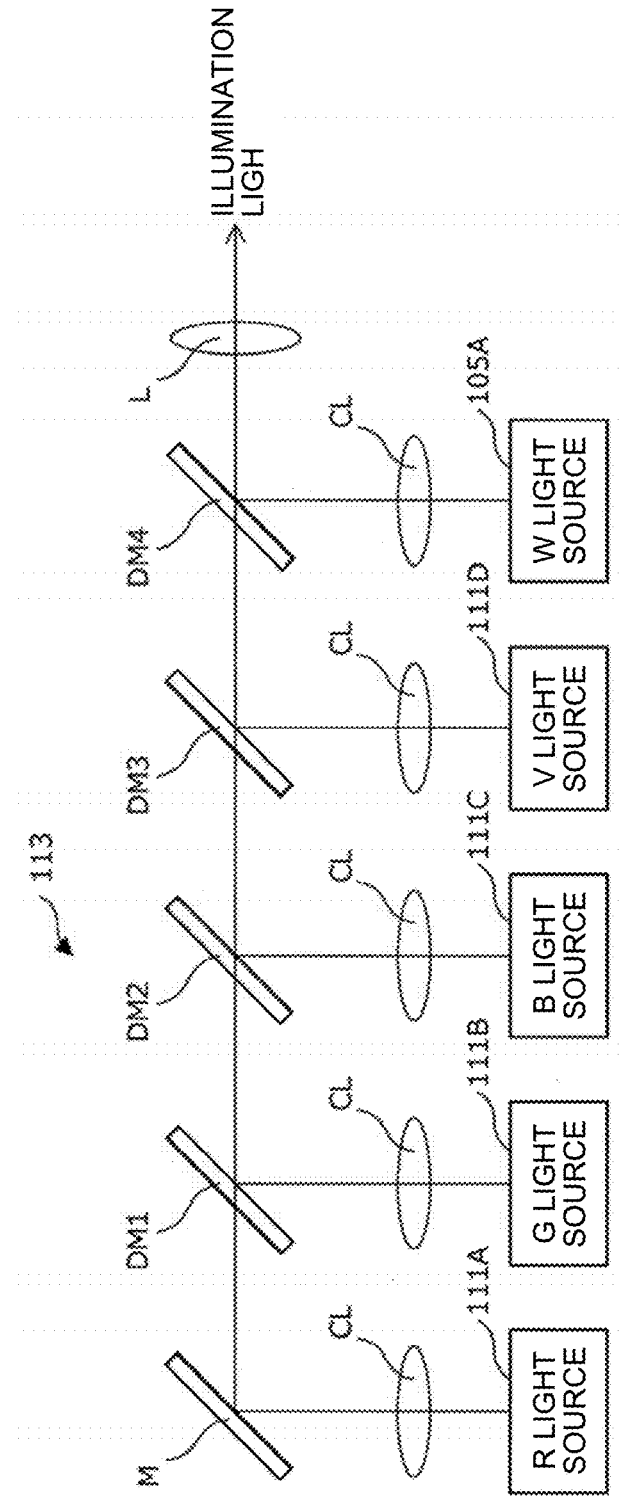
FIG. 4 is an explanatory diagram schematically illustrating an example of a multiplexing optical system in the light source unit according to the embodiment.
Figure 5:
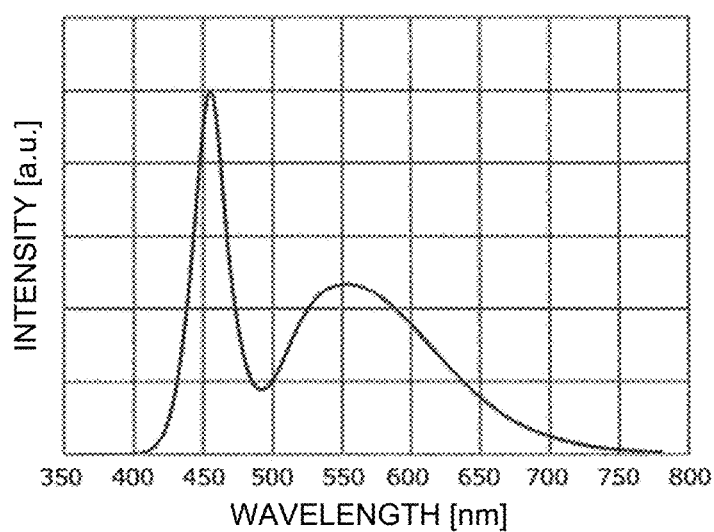
FIG. 5 is a graph illustrating an example of a spectrum of broadband light emitted from a W light source in the light source unit according to the embodiment.
Figure 6:
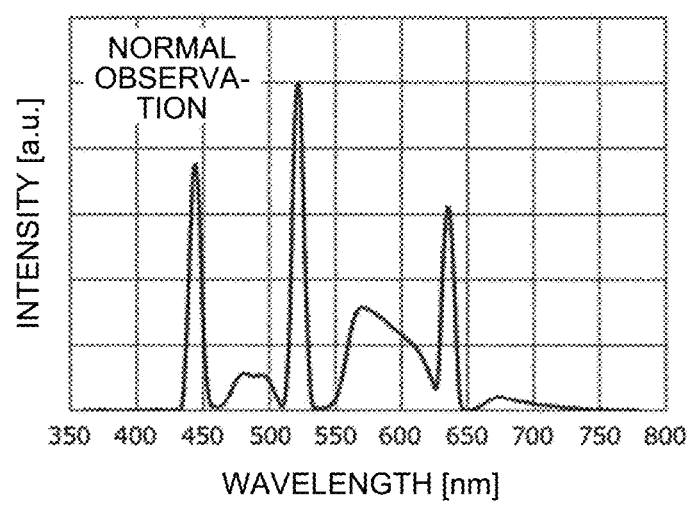
FIG. 6 is a graph illustrating an example of a spectrum of illumination light emitted from the light source unit according to the embodiment.
Figure 7:
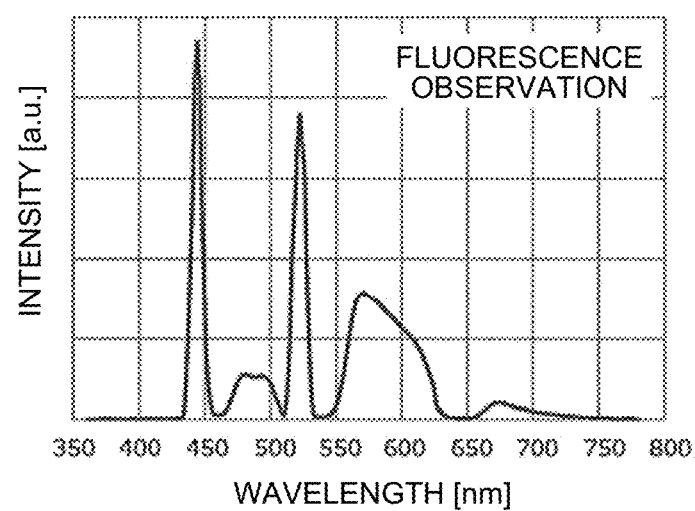
FIG. 7 is a graph illustrating an example of a spectrum of illumination light emitted from the light source unit according to the embodiment.

FIG. 3 is an explanatory diagram schematically illustrating an example of the configuration of the light source unit in the image acquisition system according to the present embodiment. FIG. 4 is an explanatory diagram schematically illustrating an example of a multiplexing optical system in the light source unit according to the present embodiment. FIG. 5 is a graph illustrating an example of a spectrum of broadband light emitted from a W light source in the light source unit according to the present embodiment. FIGS. 6 and 7 are graphs illustrating an example of a spectrum of the illumination light emitted from the light source unit according to the present embodiment.

5-ALA, which is the luminescent agent LR, emits fluorescence (red fluorescence) having a wavelength of 640 nm when irradiated with excitation light having a wavelength of 405 nm. In the light source unit 10 in a case of observing the fluorescence from 5-ALA, a white light source (W light source) 105A is provided as the broadband light source 105, as schematically illustrated in FIG. 3. Further, in the light source unit 10, a red light source (R light source) 111A, a green light source (G light source) 111B, and a blue light source (B light source) 111C are provided as the narrowband light sources, and a bluish-violet light source (V light source) 111D is provided as a light source that emits excitation light having a wavelength of 405 nm for exciting 5-ALA.

Here, as the W light source 105A, a white light emitting diode (WLED) can be used. Further, as the R light source 111A, a GaInP quantum well structure laser diode can be used, and as the G light source 111B, the B light source 111C, and the V light source 111D, a GaInN quantum well structure laser diode can be used.

Note that, since a fluorescence wavelength of 5-ALA, which is a luminescent agent LR, is 640 nm, the wavelengths of green light and blue light emitted from the G light source 111B and the B light source 111C, respectively, are not particularly specified, and light having various known wavelengths can be used. For example, the wavelength of the green light emitted from the G light source 111B can be 525 nm, and the wavelength of the blue light emitted from the B light source 111C can be 445 nm. However, in the light source unit 10 according to the present embodiment, the wavelength of red light emitted from the R light source 111A is within a range of ±30 nm (that is, 610 nm to 670 nm) of a peak fluorescence wavelength of 640 nm, preferably, a range of ±10 nm (that is, 630 nm to 650 nm) of the peak fluorescence wavelength of 640 nm, and more preferably, a range of ±5 nm (that is, 635 nm to 645 nm) of the peak fluorescence wavelength of 640 nm.

In a case of performing the normal observation by using various narrowband light sources 111A to 111D and the W light source 105A as described above, the narrowband light sources 111A to 111D (or narrowband light sources 111A to 111C) and the W light source 105A are operated. Further, in a case of observing the fluorescence from 5-ALA, the output of the R light source 111A is suppressed, and the outputs of the G light source 111B, the B light source 111C, and the W light source 105A increase or decrease so that white light having a predetermined color temperature and color coordinates is implemented by using lights from the G light source 111B, the B light source 111C, and the W light source 105A. In addition, the V light source 111D is operated as the excitation light. That is, in a case of observing the fluorescence from 5-ALA, the V light source 111D functions as the first narrowband light source 101.

As schematically illustrated in FIG. 3, the lights emitted from the respective light sources are multiplexed by a multiplexing optical system 113 to implement the illumination light, and an illumination optical system 115 irradiates a desired portion of the observation target S with the illumination light.

An example of the multiplexing optical system 113 in the light source unit 10 according to the present embodiment is schematically illustrated in FIG. 4. In the multiplexing optical system 113 illustrated in FIG. 4, the lights emitted from the respective narrowband light sources 111A to 111D are first multiplexed, and then the white light emitted from the W light source 105A is multiplexed.

The lights emitted from the respective narrowband light sources and the W light source are collimated by a collimating lens CL provided on an optical axis. The red light emitted from the R light source 111A is reflected by a mirror M at 90°, is transmitted through each of a dichroic mirror DM1, a dichroic mirror DM2, a dichroic mirror DM3, and a dichroic mirror DM4, and is collected by a condenser lens L. At this time, the red light is multiplexed with the green light emitted from the G light source 111B by the dichroic mirror DM1, is multiplexed with the blue wavelength emitted from the B light source 111C by the dichroic mirror DM2, is multiplexed with the bluish-violet light emitted from the V light source 111D by the dichroic mirror DM3, and is multiplexed with the white light emitted from the W light source 105A by the dichroic mirror DM4.

Here, the dichroic mirror DM1 has an optical characteristic of transmitting light having a red wavelength and reflecting light having a green wavelength, and the dichroic mirror DM2 has an optical characteristic of transmitting light having the red wavelength and light having the green wavelength and reflecting light having a blue wavelength. Further, the dichroic mirror DM3 has an optical characteristic of transmitting light having the red wavelength, light having the green wavelength, and light having the blue wavelength and reflecting light having a bluish-violet wavelength, and the dichroic mirror DM4 has an optical characteristic of transmitting light having the red wavelength, light having the green wavelength, light having the blue wavelength, and light having the bluish-violet wavelength, and reflecting light having a wavelength other than those.

For example, in a case where a spectrum of the white light emitted from the W light source 105A is as illustrated in FIG. 5, a light spectrum of light finally used as the illumination light is as illustrated in FIG. 6 when performing the normal observation, and is as illustrated in FIG. 7 when observing the fluorescence from 5-ALA. Note that FIGS. 6 and 7 illustrate the spectra after passing through an excitation light cut filter provided in the imaging optical system of the imaging unit 20, and thus the bluish-violet light is not included.

As is clear from comparing the spectra illustrated in FIGS. 6 and 7, the intensity of the light from the R light source 111A is suppressed when performing the fluorescence observation, and an intensity ratio of the lights emitted from the G light source 111B, the B light source 111C, and the W light source 105A, respectively, increases or decreases. In FIG. 6, as a control is performed so that the light quantity ratio of the red light, the green light, the blue light, and the white light becomes (0.25:0.4:0.3:0.5), the white light having the color temperature and color coordinates as described above is implemented. Further, in FIG. 7, as a control is performed so that the light quantity ratio of the red light, the green light, the blue light, and the white light becomes (0:0.4:0.5:1), the white light having the color temperature and color coordinates as described above is implemented.

In the light source unit 10 according to the present embodiment, not only the narrowband light source but also the broadband light source (W light source 105A) is used, such that even in a case where the quantity of light of the R light source 111A is suppressed, light belonging to a wavelength band in the vicinity of the light from the R light source 111A is emitted from the broadband light source (W light source 105A). Therefore, even in a case where the quantity of light of the R light source 111A is suppressed, the white light having the color temperature and color coordinates as described above can be implemented by using the lights from the G light source 111B, the B light source 111C, and the W light source 105A.

Note that the configuration of the multiplexing optical system 113 is not limited to that illustrated in FIG. 4, and various known multiplexing methods can be adopted. A face-to-face multiplexing method may be adopted, or other methods may be adopted.

The illumination optical system 115 provided at the subsequent stage irradiates a desired portion of the observation target S with the illumination light obtained by multiplexing performed by the multiplexing optical system 113 so as to have a desired color temperature and color coordinates. The illumination optical system 115 is configured by using known optical elements such as various lenses or mirrors, and is not particularly limited, and various known optical systems can be appropriately adopted. For example, in a case where the image acquisition system 1 according to the present embodiment is mounted on a medical endoscope, various known endoscope optical systems provided in a medical endoscope unit can be adopted as the illumination optical system 115, and in a case where the image acquisition system 1 according to the present embodiment is mounted on a medical microscope, various known microscope optical systems provided in a medical microscope unit can be adopted as the illumination optical system 115.

Hereinabove, a specific example of the light source unit 10 has been described in detail with reference to FIGS. 3 to 7.

Note that, in a case where fluorescein is used as the luminescent agent LR, fluorescein is excited by light having a wavelength of 445 nm and emits fluorescence (green fluorescence) having a wavelength of 520 nm. Therefore, in a case of using fluorescein, the B light source 111C functions as the first narrowband light source 101 by setting the wavelength of the blue light emitted from the B light source 111C to 445 nm. Further, the wavelength of the green light emitted from the G light source 111B that functions as the second narrowband light source 103 is within a range of ±30 nm (that is, 490 nm to 550 nm) of a peak fluorescence wavelength of 520 nm, preferably, a range of ±10 nm (that is, 510 nm to 530 nm) of the peak fluorescence wavelength of 520 nm, and more preferably, a range of ±5 nm (that is, 515 nm to 525 nm) of the peak fluorescence wavelength of 520 nm. Then, when performing the normal observation, the R light source 111A, the G light source 111B, the B light source 111C, and the W light source 105A are operated, and when performing the fluorescence observation, the output of the G light source 111B is suppressed, and the outputs of the R light source 111A, the B light source 111C, and the W light source 105A increase or decrease so that white light having a predetermined color temperature and color coordinates is implemented by using the lights from the R light source 111A, the B light source 111C, and the W light source 105A.

Similarly, even in a case where Laserphyrin is used as the luminescent agent LR, a light source that emits appropriate excitation light may be provided as the first narrowband light source 101, and a wavelength of light emitted from a narrowband light source that emits light in a wavelength band corresponding to fluorescence from Laserphyrin may be within a range of ±30 nm of a peak fluorescence wavelength of Laserphyrin.

Further, even in a case where a plurality of luminescent agent LRs are used in combination, the first narrowband light source 101 that functions as the excitation light may be appropriately provided in consideration of an excitation wavelength and a peak light emission wavelength of each luminescent agent LR, and a wavelength of narrowband light emitted from a narrowband light source that functions as the second narrowband light source 103 may be within a range of ±30 nm of the peak light emission wavelength.

<Example of Detailed Configuration of Imaging Unit 20>

In the following, the imaging unit 20 in the image acquisition system 1 according to the present embodiment in a case where, for example, 5-ALA is used as the luminescent agent LR, will be described in detail with reference to FIGS. 8 to 10B.

FIG. 8 is an explanatory diagram schematically illustrating an example of the configuration of the imaging unit in the image acquisition system according to the present embodiment. FIGS. 9A to 10B are explanatory diagram schematically illustrating the example of the imaging optical system in the imaging unit according to the present embodiment.

As illustrated in FIG. 8, the imaging unit 20 according to the present embodiment includes at least the first image sensor 201 and the second image sensor 203. Further, it is preferable that the imaging unit 20 according to the present embodiment further includes an imaging optical system 211 for guiding the light from the observation target S to the first image sensor 201 and the second image sensor 203. By further including such an imaging optical system 211, it becomes possible to more surely form an image of the light from the observation target S on the first image sensor 201 and the second image sensor 203.

Here, image sensors used as the first image sensor 201 and the second image sensor 203 are not particularly limited, and for example, various known image sensors such as a complementary metal-oxide-semiconductor (CMOS) sensor or a charge-coupled device (CCD) sensor can be used.

Further, the image sensors used as the first image sensor 201 and the second image sensor 203 are preferably image sensors for color imaging with, for example, a Bayer array. Further, in some cases, it is also possible to use an image sensor for monochrome imaging as the image sensor that functions as the first image sensor 201.

In the imaging unit 20 according to the present embodiment, as mentioned earlier, the first captured image obtained from the first image sensor 201 is an image obtained by capturing an image in a wavelength band (that is, the light emission wavelength band) corresponding to the light emitted from the luminescent agent LR, and the second captured image obtained from the second image sensor 203 is an image obtained by capturing an image in a wavelength band (that is, a wavelength band other than the light emission wavelength band) that does not include a wavelength corresponding to the light emitted from the luminescent agent LR.

The imaging optical system 211 preferably provided in the imaging unit 20 according to the present embodiment is an optical system for guiding the light from the observation target S to the first image sensor 201 and the second image sensor 203. As the imaging optical system 211, for example, various optical systems provided in a medical microscope unit, a medical endoscope unit, or the like can be appropriately used.

Further, it is preferable that the imaging optical system 211 according to the present embodiment further includes a branching optical system that makes the light from the observation target S branch into light in the light emission wavelength band and light in a wavelength band other than the light emission wavelength band. Since the imaging optical system 211 further includes the branching optical system as described above, the light from the observation target S can be more surely separated into the light in the light emission wavelength band and the light in the wavelength band other than the light emission wavelength band, it is possible to further improve the signal-to-noise ratio of the captured image obtained from each of the first image sensor 201 and the second image sensor 203.

Figure 9A:
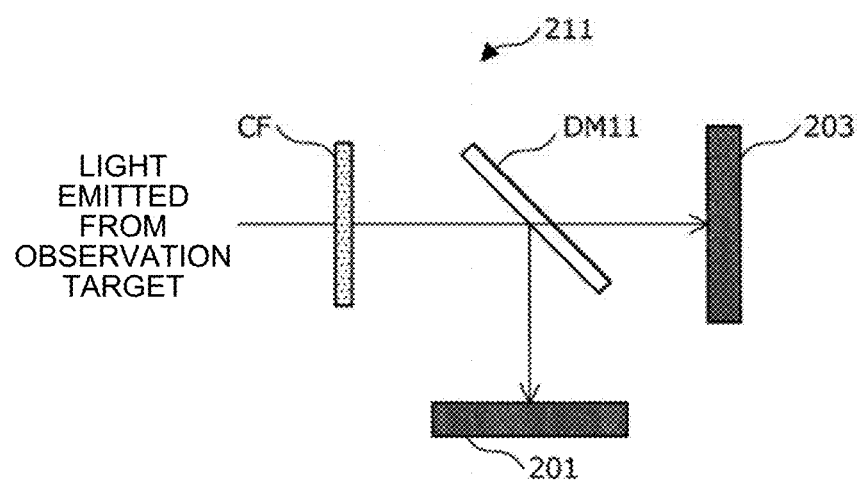
FIG. 9A is an explanatory diagram schematically illustrating an example of an imaging optical system in the imaging unit according to the embodiment.
Figure 9B:
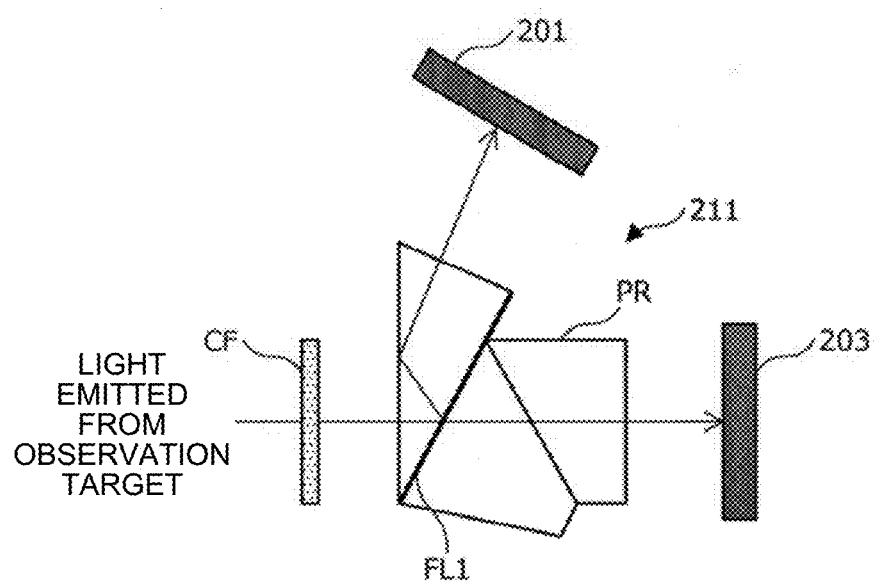
FIG. 9B is an explanatory diagram schematically illustrating the example of the imaging optical system in the imaging unit according to the embodiment.

An example of the imaging optical system is illustrated in FIGS. 9A and 9B. In FIG. 9A, an excitation light cut filter CF and a dichroic mirror DM11 that functions as the branching optical system are provided as optical elements constituting the imaging optical system 211.

The excitation light cut filter CF is provided in the image acquisition system 1 according to the present embodiment as needed in order to prevent the excitation light emitted from the first narrowband light source 101 from being guided to the first image sensor 201 and the second image sensor 203 in a case of observing the light emitted from the luminescent agent LR. It is preferable that the excitation light cut filter CF is provided so as to be detachable from an optical path of the imaging optical system 211, and is arranged on the optical path as needed. Such an excitation light cut filter CF is not particularly limited, and various known wavelength selection filters and the like can be appropriately used.

Further, in the example illustrated in FIG. 9A, in the dichroic mirror DM11 functioning as the branching optical system, a wavelength selection filter having an optical characteristic of reflecting light belonging to the light emission wavelength band to make an image of the light be formed on the first image sensor 201, and transmitting light belonging to a wavelength band other than the light emission wavelength band to make an image of the light be formed on the second image sensor 203 is provided. For example, in a case where 5-ALA is used as the luminescent agent LR, the wavelength selection filter provided in the dichroic mirror DM11 has an optical characteristic of reflecting light (for example, light in a range of 640 nm±10 nm) near 640 nm which is the fluorescence wavelength of 5-ALA, and transmitting light in other wavelength bands.

Further, in the imaging optical system 211 according to the present embodiment, for example, as illustrated in FIG. 9B, a color separation prism PR including a plurality of prisms may be used instead of the dichroic mirror DM11. In the color separation prism PR, a wavelength selection filter FL1 is provided on a junction surface between a prism positioned at the first position on the upstream side of the optical path and a prism positioned at the second position, and the wavelength selection filter FL1 has the same optical characteristic as in FIG. 9A. By using one color separation prism PR as illustrated in FIG. 9B as the branching optical system, it is possible to use up to three image sensors, and to separate the light from the observation target S into three luminous fluxes.

Figure 10A:
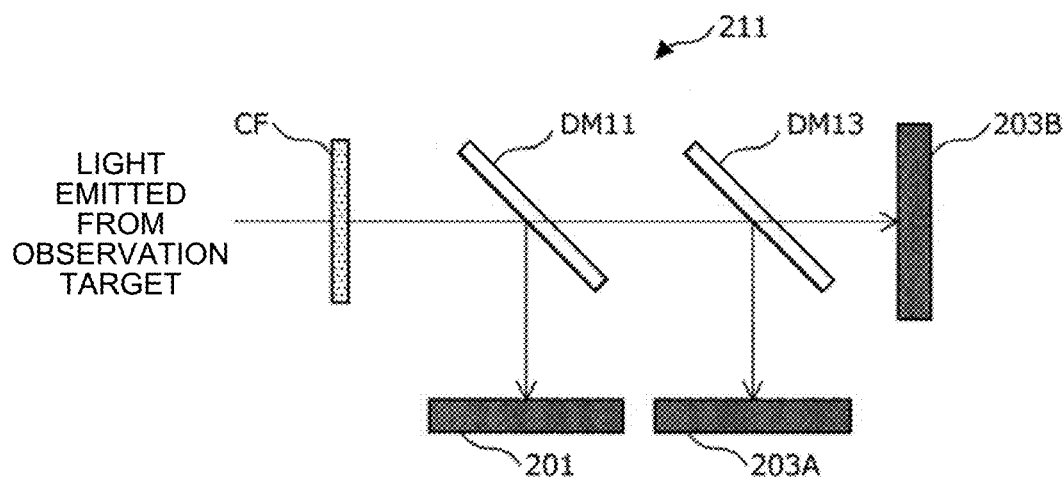
FIG. 10A is an explanatory diagram schematically illustrating an example of the imaging optical system in the imaging unit according to the embodiment.

Further, in the imaging optical system 211 according to the present embodiment, the image sensor functioning as the second image sensor 203 may be constituted by one image sensor or a plurality of image sensors. As illustrated in FIG. 10A, for example, as two dichroic mirrors DM11 and DM13 are used, it is possible to further separate light in a wavelength band other than the light emission wavelength band for each of image sensors 203A and 203B which function as the second image sensor 203 by using the dichroic mirror DM13.

Figure 10B:
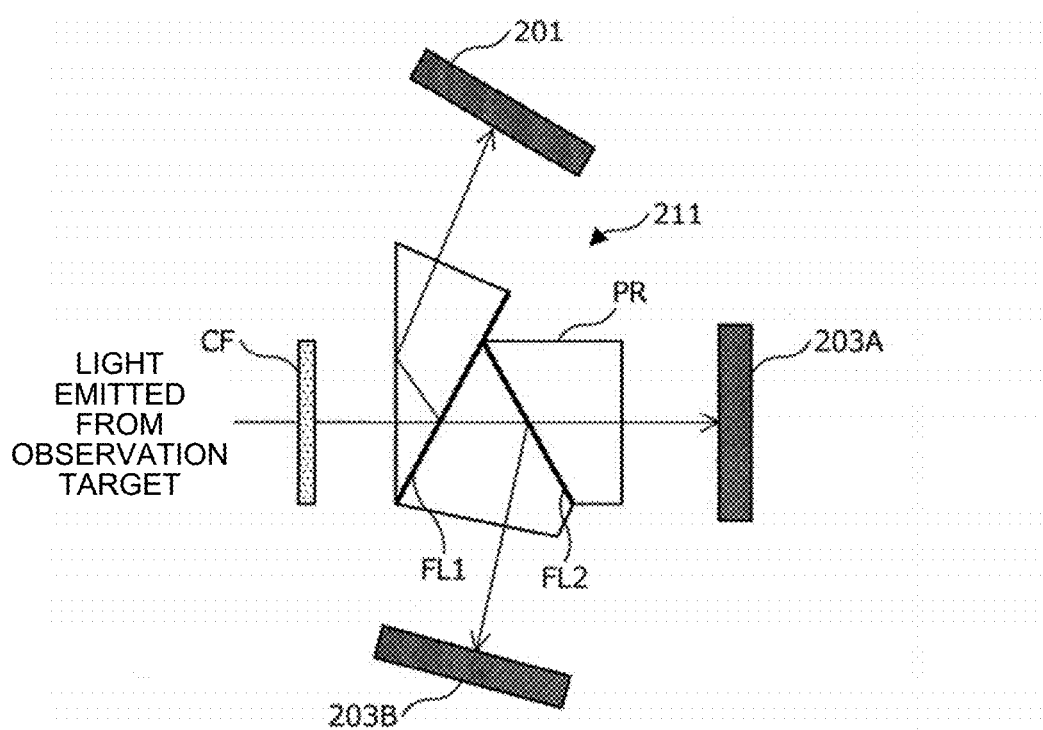
FIG. 10B is an explanatory diagram schematically illustrating the example of the imaging optical system in the imaging unit according to the embodiment.

Further, as illustrated in FIG. 10B, in the color separation prism PR, as a wavelength selection filter FL2 is further provided on a junction surface between a prism positioned at the second position and a prism positioned at the third position when viewed from the upstream side of the optical path, it is possible to further separate the light in a wavelength band other than the light emission wavelength band for each of the image sensors 203A and 203B that function as the second image sensor 203.

In this way, by using a plurality of dichroic mirrors or by using a color separation prism in which a plurality of prisms are combined, it is possible to separate the light from the observation target S into three or more optical paths. As a result, for example, in a case of observing lights emitted from a plurality of luminescent agent LRs at the same time, it is possible to separate lights emitted from the plurality of luminescent agents LR and allow different image sensors to capture images of the lights by appropriately adjusting the optical characteristic of the wavelength selection filter.

In the imaging unit 20 according to the present embodiment, the image sensor functioning as the first image sensor 201 and the image sensor functioning as the second image sensor 203 change according to the wavelength of the light emitted from the luminescent agent LR that is focused on. Therefore, for example, in the imaging unit 20 as illustrated in FIG. 10A, for a certain luminescent agent LR1, the image sensor denoted by Reference Sign 201 functions as the first image sensor, but for another luminescent agent LR2, the image sensor denoted by Reference Sign 203A may function as the first image sensor.

Hereinabove, the imaging unit 20 according to the present embodiment has been described in detail with reference to FIGS. 8 to 10B.

<Example of Configuration of Arithmetic Processing Unit>

Figure 12:
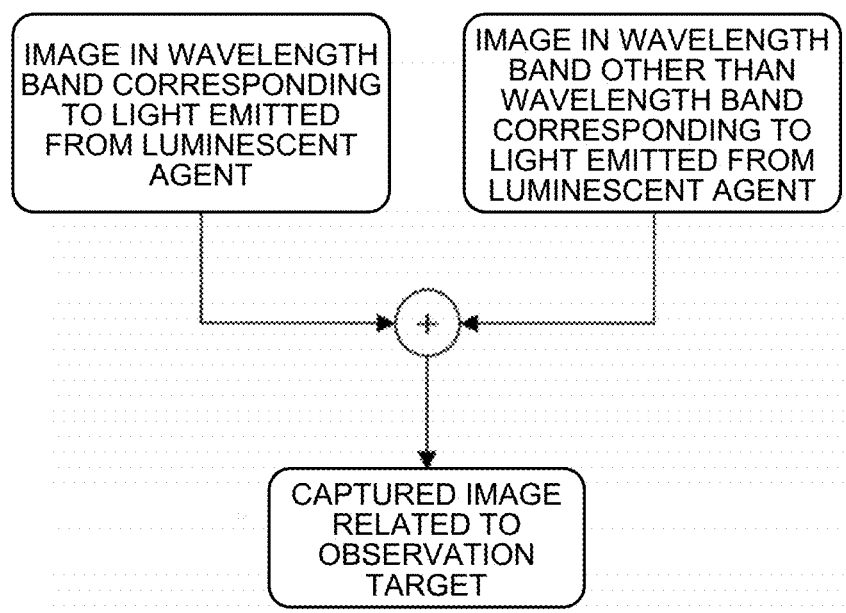
FIG. 12 is an explanatory diagram for describing an image processing method performed in the arithmetic processing unit according to the embodiment.

Next, an example of a configuration of the arithmetic processing unit 30 included in the image acquisition system 1 according to the present embodiment will be described with reference to FIGS. 11 and 12. FIG. 11 is a block diagram illustrating an example of the configuration of the arithmetic processing unit in the image acquisition system according to the present embodiment, and FIG. 12 is an explanatory diagram for describing an image processing method performed in the arithmetic processing unit according to the present embodiment.

The arithmetic processing unit 30 according to the present embodiment comprehensively controls the operating states of the light source unit 10 and the imaging unit 20. Further, the arithmetic processing unit 30 according to the present embodiment uses two types of captured images (the first captured image and the second captured image) output from the imaging unit 20 to generate a captured image related to the observation target S, and provides the obtained captured image to the user of the image acquisition system 1.

As schematically illustrated in FIG. 11, the arithmetic processing unit 30 having such a function mainly includes an imaging processing control unit 301, a data acquisition unit 303, an image processing unit 305, an output control unit 307, a display control unit 309, and a storage unit 311.

The imaging processing control unit 301 is implemented by, for example, a central processing unit (CPU), a read only memory (ROM), a random access memory (RAM), an input device, a communication device, and the like. The imaging processing control unit 301 is a processing unit that controls the operating states of the light source unit 10 and the imaging unit 20 according to an input operation performed by a doctor or the like who is the user.

For example, the imaging processing control unit 301 can control each light source provided in the light source unit 10 to control the on/off state of each light source or the intensity (the quantity of light) of light emitted from each light source. Such a control of the light source can be implemented, for example, by controlling the magnitude of a drive voltage applied to each light source. As a result, the imaging processing control unit 301 can implement the illumination light having the predetermined color temperature and color coordinates as described above. Note that, when controlling the light source unit 10, the imaging processing control unit 301 preferably controls the operating state of each light source provided as the light source unit 10 independently of each other, as described above.

Further, the imaging processing control unit 301 can control the operating state of each image sensor provided in the imaging unit 20 to perform various controls such as synchronization between an irradiation timing of the illumination light from the light source unit 10 and an imaging timing of each image sensor in the imaging unit 20. Further, the imaging processing control unit 301 can appropriately control the gain, white balance, or the like of each image sensor provided in the imaging unit 20 to achieve a desired state. As a result, it is possible for each image sensor to generate a captured image having a more excellent signal-to-noise ratio.

In addition to the above-described control, the imaging processing control unit 301 can perform various known controls that can be performed with respect to the light source unit 10 and the imaging unit 20.

In addition, the imaging processing control unit 301 can appropriately output information indicating the operating states of the light source unit 10 and the imaging unit 20 to the data acquisition unit 303 or the image processing unit 305. As a result, in the data acquisition unit 303 or the image processing unit 305, it is possible to easily determine from which image sensor the first captured image is obtained, from which image sensor the second captured image is obtained, and the like.

The data acquisition unit 303 is implemented by, for example, a CPU, a ROM, a RAM, a communication device, or the like. The data acquisition unit 303 acquires data of the captured images (that is, the first captured image and the second captured image) output from the respective image sensors provided in the imaging unit 20. The data of the captured images output from the respective image sensors is output to the image processing unit 305 provided at the subsequent stage, the data being acquired by the data acquisition unit 303. Further, the data acquisition unit 303 associates the data of the respective captured images output from the imaging unit 20 with time information related to the date and time when the data is acquired, and stores it as history information in the storage unit 311 or the like provided at the subsequent stage.

The image processing unit 305 is implemented by, for example, a CPU, a graphics processing unit (GPU), a ROM, a RAM, and the like. The image processing unit 305 generates a captured image related to the observation target S by using the first captured image output from the image sensor functioning as the first image sensor 201 and the second captured image output from the image sensor functioning as the second image sensor 203. More specifically, as schematically illustrated in FIG. 12, the image processing unit 305 generates a captured image related to the observation target S by combining the first captured image, which is a captured image in a wavelength band (light emission wavelength band) corresponding to light emitted from the luminescent agent, and the second captured image, which is a captured image in a wavelength band other than the wavelength band corresponding to the light emitted from the luminescent agent with each other. Since the first image sensor 201 and the second image sensor 203 capture images of the same field of view of the observation target S, it is possible to easily generate a composite image by combining the first captured image and the second captured image with each other.

For example, in a case where 5-ALA is introduced as the luminescent agent LR into the observation target S and an operation when performing the normal observation is indicated by the user, only an image of a wavelength component that is not in a red wavelength band is formed on the image sensor functioning as the second image sensor 203. Therefore, in a case where only the second captured image obtained from the second image sensor 203 is used, a correct color image cannot be generated. However, although a correct color image cannot be developed only with a signal in the red wavelength band CMOS1, an image of a component in the red wavelength band is formed on the image sensor functioning as the first image sensor 201. Therefore, it is possible to generate a correct color image by combining the first captured image and the second captured image. More specifically, the image processing unit 305 generates a normal color captured image by combining a signal of an R component constituting the first captured image and signals of a G component and a B component constituting the second captured image.

For example, in a case where 5-ALA is introduced as the luminescent agent LR into the observation target S and an operation when performing the fluorescence observation is indicated by the user, an image of fluorescence of 5-ALA is formed on the image sensor functioning as the first image sensor 201, and an image of a component other than the fluorescence of 5-ALA is not formed. As a result, it is possible to significantly improve the signal-to-noise ratio of the first captured image. Further, it is possible to obtain, from the image sensor functioning as the second image sensor 203, a background image that is equivalent to that when performing the normal observation, by adjusting the color temperature and color coordinates of the illumination light as described above. Therefore, it is possible to obtain a color captured image of the observation target S, in which the fluorescence of 5-ALA is superimposed, by combining the first captured image and the second captured image.

At this time, in order to make it easier for the user to recognize the light emitted from the luminescent agent LR, the image processing unit 305 may combine the captured image with the second captured image after converting a color of the light emitted from the luminescent agent LR into a color (for example, green in a case where the observation target S is a living tissue) that does not exist in the observation target S, regardless of the color of the emitted light. By doing so, the user can easily recognize a portion where the emitted light exists in the captured image that is generated.

Note that, in a case where the illumination light is constituted by only the broadband light (white light) from the W light source 105A, an image of a component in the red wavelength band, which is included in the illumination light, is formed on the image sensor functioning as the first image sensor 201, and thus, in addition to the fluorescence of 5-ALA, the image of the component in the red wavelength band, which is included in the illumination light, is formed on the first image sensor 201, which results in a decrease in the signal-to-noise ratio of the first captured image.

Once the captured image related to the observation target S is generated as described above, the image processing unit 305 outputs data of the generated captured image to the output control unit 307. In addition, the image processing unit 305 may associate the data of the generated captured image with time information such as the date and time when the data is generated, and then store it as history information in the storage unit 311 or the like.

The output control unit 307 is implemented by, for example, a CPU, a ROM, a RAM, an output device, a communication device, or the like. The output control unit 307 controls the output of the data of the captured image related to the observation target S, the captured image being generated by the image processing unit 305. For example, the output control unit 307 may output the data of the captured image related to the observation target S via an output device such as a printer, and provide, to the user, the output data as a paper medium, or may output the data of the captured image related to the observation target S to various recording media, the captured image being generated by the image processing unit 305. Further, the output control unit 307 may cause various information processing devices such as a computer, a server, and a process computer provided externally to output the data of the captured image related to the observation target S, the captured image being generated by the image processing unit 305, thereby sharing image data. Further, the output control unit 307 may cause a display device such as various displays included in the image acquisition system 1, or a display device such as various displays provided outside the image acquisition system 1 to output the data of the captured image related to the observation target S, in cooperation with the display control unit 309 as described later, the captured image being calculated by the image processing unit 305.

The display control unit 309 is implemented by, for example, a CPU, a ROM, a RAM, an output device, a communication device, or the like. The display control unit 309 performs a display control when displaying the captured image related to the observation target S or various information regarding the captured image on an output device such as a display or the like included in the image acquisition system 1, or an output device provided outside the image acquisition system 1, the captured image being generated by the image processing unit 305. As a result, the user of the image acquisition system 1 can grasp various information regarding the observation target that is focused on, on the spot.

The storage unit 311 is implemented by, for example, a RAM or a storage device included in the arithmetic processing unit 30. The storage unit 311 stores various databases, software programs, and the like used when the imaging processing control unit 301 or the image processing unit 305 performs various processing. Further, in the storage unit 311, various setting information in various control processing performed by the imaging processing control unit 301 or various image processing performed by the image processing unit 305, various parameters that need to be stored when the arithmetic processing unit 30 according to the present embodiment performs any processing, the progress of the processing, and the like are appropriately recorded. The imaging processing control unit 301, the data acquisition unit 303, the image processing unit 305, the output control unit 307, the display control unit 309, and the like can freely perform data read/write processing on the storage unit 311.

Hereinabove, an example of the functions of the arithmetic processing unit 30 according to the present embodiment has been described. Each component described above may be configured by using a general-purpose member or circuit, or may be configured by hardware specialized for the function of each component. Further, all the functions of each component may be performed by a CPU or the like. Therefore, it is possible to appropriately change the configuration to be used according to the technical level at the time of implementing the present embodiment.

Note that it is possible to create a computer program for implementing each function of the arithmetic processing unit according to the present embodiment as described above and install the computer program in a personal computer or the like. Further, it is possible to provide a computer-readable recording medium in which such a computer program is stored. Examples of the recording medium include a magnetic disk, an optical disk, a magneto-optical disk, and a flash memory. Further, the computer program described above may be distributed via, for example, a network without using the recording medium.

<Example of Hardware Configuration of Arithmetic Processing Unit>

Figure 13:
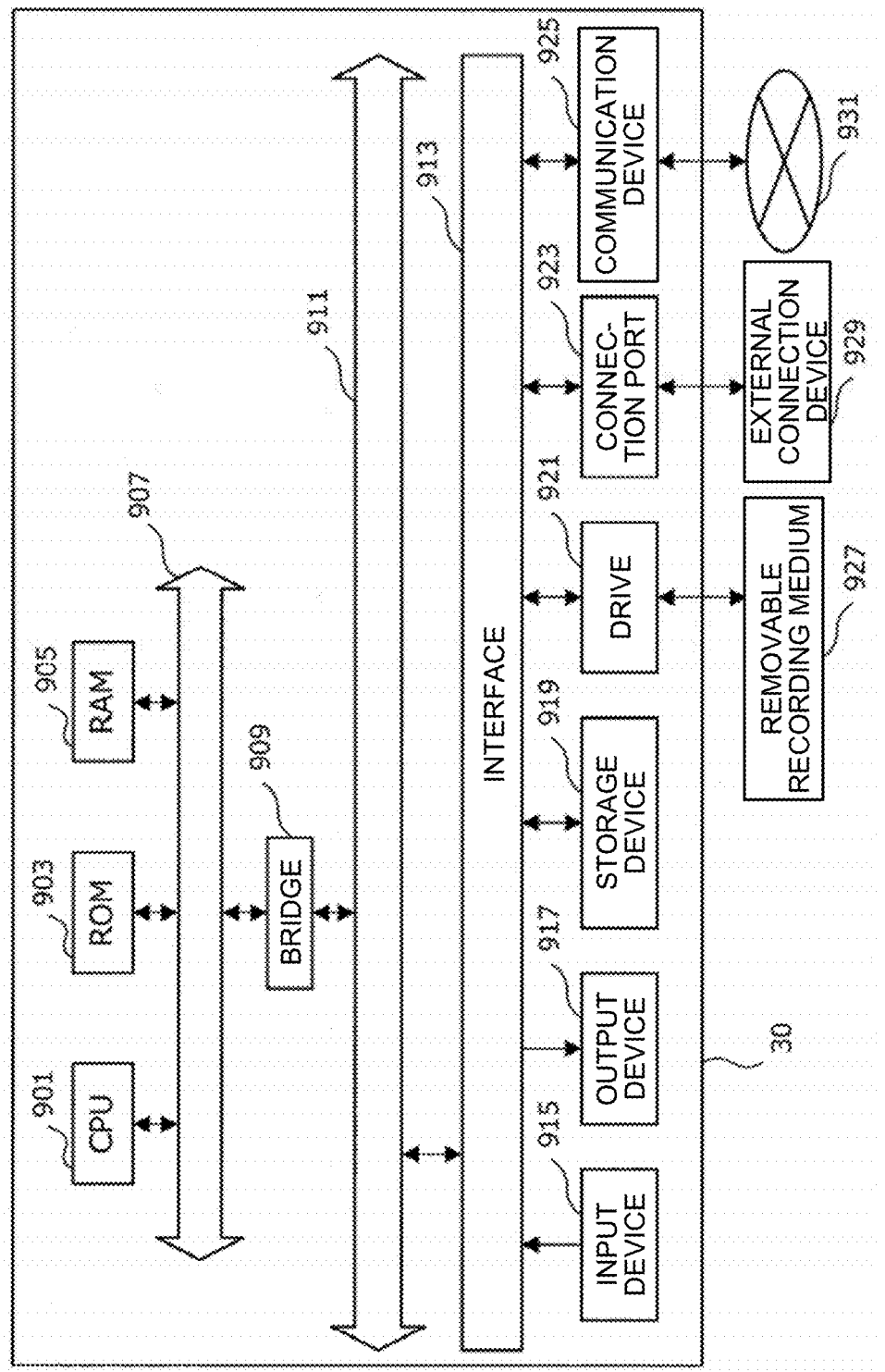
FIG. 13 is a block diagram illustrating an example of a hardware configuration of the arithmetic processing unit according to the embodiment.

Next, the hardware configuration of the arithmetic processing unit 30 according to the embodiment of the present disclosure will be described in detail with reference to FIG. 13. FIG. 13 is a block diagram for describing the hardware configuration of the arithmetic processing unit 30 according to the embodiment of the present disclosure.

The arithmetic processing unit 30 mainly includes a CPU 901, a ROM 903, and a RAM 905. In addition, the arithmetic processing unit 30 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing device or a control device, and controls an overall operation in the arithmetic processing unit 30 or a part thereof according to various programs recorded in the ROM 903, the RAM 905, the storage device 919, or a removable recording medium 927. The ROM 903 stores a program, a calculation parameter, and the like used by the CPU 901. The RAM 905 primarily stores the program used by the CPU 901, a parameter that changes as appropriate during execution of the program, and the like. These are connected to each other by the host bus 907 configured by using an internal bus such as a CPU bus.

The host bus 907 is connected to the external bus 911 such as a peripheral component interconnect/interface (PCI) bus via the bridge 909.

The input device 915 is an operating means operated by the user, such as a mouse, a keyboard, a touch panel, a button, a switch, or a lever. Further, the input device 915 may be, for example, a remote control means (so-called remote controller) using infrared rays or other radio waves, or may be an external connection device 929 such as a mobile phone or PDA that supports the operation of the arithmetic processing unit 30. In addition, the input device 915 is configured by using, for example, an input control circuit that generates an input signal on the basis of information input by the user using the above operating means and outputs the input signal to the CPU 901. By operating the input device 915, the user can input various data to the arithmetic processing unit 30 and instruct a processing operation.

The output device 917 is configured by using a device capable of visually or audibly notifying the user of acquired information. Examples of such a device include a display device such as a CRT display device, a liquid crystal display device, a plasma display device, or an EL display device or lamp, an audio output device such as a speaker and a headphone, a printer device, a mobile phone, or a facsimile. The output device 917 outputs, for example, a result obtained by various processing performed by the arithmetic processing unit 30. Specifically, the display device displays the result obtained by various processing performed by the arithmetic processing unit 30 as text or an image. On the other hand, the audio output device converts an audio signal composed of reproduced audio data, acoustic data, or the like into an analog signal and outputs the analog signal.

The storage device 919 is a data storage device configured as an example of the storage unit of the arithmetic processing unit 30. The storage device 919 is configured by using, for example, a magnetic storage device such as a hard disk drive (HDD), a semiconductor storage device, an optical storage device, or a magneto-optical storage device. The storage device 919 stores a program executed by the CPU 901, various data, various data acquired from the outside, and the like.

The drive 921 is a reader/writer for a recording medium, and is built in or externally attached to the arithmetic processing unit 30. The drive 921 reads information recorded in the removable recording medium 927 such as the mounted magnetic disk, optical disk, magneto-optical disk, or semiconductor memory, and outputs the information to the RAM 905. Further, the drive 921 can also write a record in the removable recording medium 927 such as the mounted magnetic disk, optical disk, magneto-optical disk, or semiconductor memory. Examples of the removable recording medium 927 include a DVD medium, an HD-DVD medium, and a Blu-ray (registered trademark) medium. Further, the removable recording medium 927 may be a compact flash (CF) (registered trademark), a flash memory, a secure digital (SD) memory card, or the like. Further, the removable recording medium 927 may be, for example, an integrated circuit (IC) card or electronic device that is equipped with a non-contact type IC chip.

The connection port 923 is a port for directly connecting a device to the arithmetic processing unit 30. Examples of the connection port 923 include a universal serial bus (USB) port, an IEEE1394 port, and a small computer system interface (SCSI) port. Other examples of the connection port 923 include an RS-232C port, an optical audio terminal, and a high-definition multimedia interface (HDMI) (registered trademark) port. By connecting the external connection device 929 to the connection port 923, the arithmetic processing unit 30 acquires various data directly from the external connection device 929 and provides various data to the external connection device 929.

The communication device 925 is, for example, a communication interface configured by using a communication device or the like for connection to a communication network 931. The communication device 925 is, for example, a communication card for a wired or wireless local area network (LAN), Bluetooth (registered trademark), wireless USB (WUSB), or the like. Further, the communication device 925 may be a router for optical communication, a router for asymmetric digital subscriber line (ADSL), a modem for various types of communication, or the like. The communication device 925 can transmit and receive a signal and the like to and from, for example, the Internet and another communication device in accordance with a predetermined protocol such as TCP/IP. Further, the communication network 931 connected to the communication device 925 is configured by using a network or the like connected in a wire or wireless manner, and may be, for example, the Internet, a home LAN, infrared communication, radio wave communication, or satellite communication.

Hereinabove, an example of the hardware configuration capable of implementing the functions of the arithmetic processing unit 30 according to the embodiment of the present disclosure has been described. Each component described above may be configured by using a general-purpose member, or may be configured by hardware specialized for the function of each component. Therefore, it is possible to appropriately change the hardware configuration to be used according to the technical level at the time of implementing the present embodiment.

<Image Acquisition Method>

Figure 14:
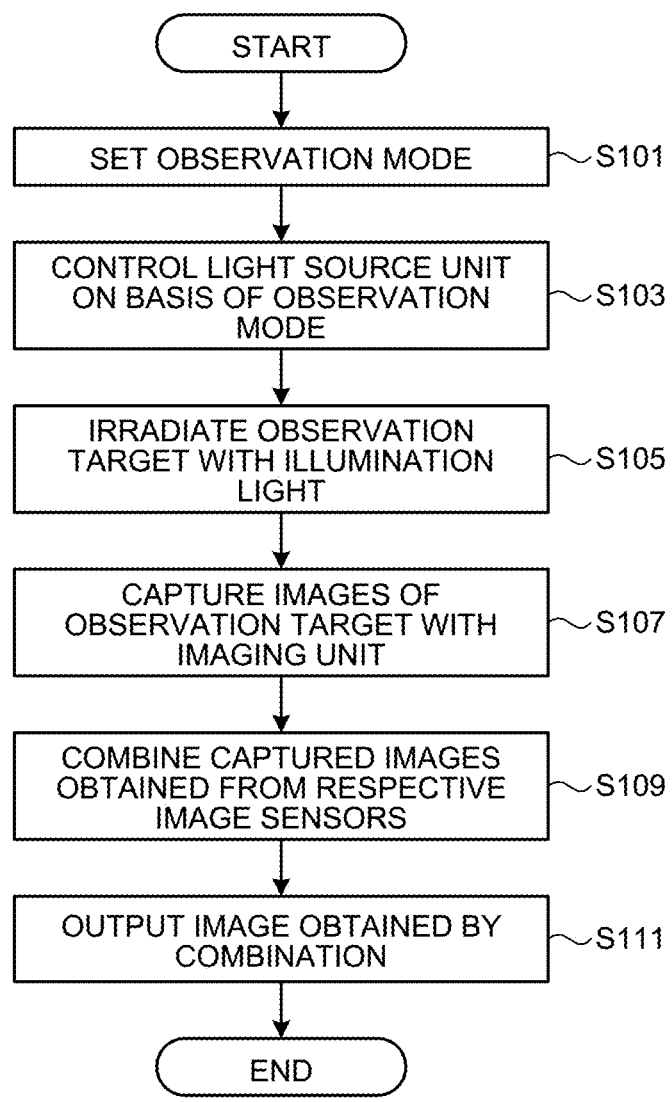
FIG. 14 is a flowchart illustrating an example of a flow of an image acquisition method according to the embodiment.

Next, an example of a flow of an image acquisition method using the image acquisition system 1 as described above will be briefly described with reference to FIG. 14. FIG. 14 is a flowchart illustrating an example of the flow of the image acquisition method according to the present embodiment.

First, the user sets an observation mode (that is, whether to perform the normal observation using the illumination light in the visible light wavelength band or to observe the light emitted from the luminescent agent) for the image acquisition system 1 as described above (Step S101). Then, the imaging processing control unit 301 provided in the arithmetic processing unit 30 of the image acquisition system 1 controls the light source unit 10 on the basis of the set observation mode (Step S103) to implement illumination light in a desired state.

Under the control of the arithmetic processing unit 30, the light source unit 10 of the image acquisition system 1 irradiates the observation target with illumination light suitable for the observation mode (Step S105), and the imaging unit 20 of the image acquisition system 1 captures an image of the observation target under the control of the arithmetic processing unit 30 (Step S107). Respective image sensors provided in the imaging unit 20 output, to the arithmetic processing unit 30, captured images that are generated.

The arithmetic processing unit 30 of the image acquisition system 1 combines the captured images obtained from the respective image sensors (Step S109) to obtain a captured image related to the observation target. Then, the arithmetic processing unit 30 outputs the obtained captured image related to the observation target (Step S111). As a result, the user of the image acquisition system 1 can obtain a captured image related to the observation target that is focused on.

As described above, an example of the flow of the image acquisition method according to the present embodiment has been briefly described with reference to FIG. 14.

<Conclusion>

As described above, by using the image acquisition system and the image acquisition method according to the present embodiment, even in a case where a wavelength of light emitted from light emitted from the luminescent agent belongs to the visible light wavelength band, it is possible to acquire a luminescence image without causing a decrease in the signal-to-noise ratio of the luminescence image, causing a decrease in frame rate at the time of imaging, and causing blinking of a light source.

Further, in the image acquisition system according to the present embodiment as described above, it is possible to switch between the normal observation and observation of the light emitted from the luminescent agent without changing the hardware configuration of the system, and thus the convenience of the user is further improved.

Further, by extending the configurations of the light source unit 10 and the imaging unit 20 of the image acquisition system according to the present embodiment as described above, not only observation using one luminescent agent but also observation using a plurality of luminescent agents can be performed.

In a case of using a captured image with a low signal-to-noise ratio, which is generated in a state where the illumination light and the light emitted from the luminescent agent are mixed, the functions of luminescence imaging such as tumor identification and area identification cannot be fully exerted, and thus misdiagnosis or misjudgment by a doctor or the like may be caused. However, by using the image acquisition system and the image acquisition method according to the present embodiment, it is possible to simultaneously obtain a luminescence image having an excellent signal-to-noise ratio and a normal captured image, and thus a luminescence image having a background color can be provided to the user. Therefore, the user can perform a surgical operation while viewing the luminescence image without performing operations such as screen switching and light source switching. In addition, since the screen switching operation is not required, the user can gaze at one screen, which leads to a reduction of stress of the user. Further, since the light source switching is usually performed by hardware switching such as switching of an optical filter, the number of components of a device can be reduced.

Further, by using the image acquisition system according to the present embodiment, it is possible to implement luminescence imaging using a plurality of luminescent agents. As a result, it is possible to perform operations that could not be performed until now, such as performing blood vessel identification with ICG and removing a tumor while identifying the tumor with 5-ALA.

Examples

Next, the image acquisition system and the image acquisition method according to the present disclosure will be specifically described with reference to Examples. It should be noted that the following Examples are merely examples of the image acquisition system and the image acquisition method according to the present disclosure, and the image acquisition system and the image acquisition method according to the present disclosure are not limited to the following examples.

In each of the following Examples, a simulation was performed on the basis of a spectrum of illumination light emitted from the light source unit 10 and an optical characteristic of the wavelength selection filter provided in the branching optical system of the imaging unit 20 in a case of observing light emitted from a luminescent agent introduced into a living tissue by using the image acquisition system 1 including the light source unit 10 as illustrated in FIG. 3, and it was verified how much the signal-to-noise ratio improves.

Note that it was assumed that the red light has a wavelength of 638 nm, the green light has a wavelength of 525 nm, and the blue light has a wavelength of 445 nm. Further, it was assumed that the broadband light is white light having the spectrum illustrated in FIG. 5. In addition, a similar simulation was performed even in a case where only white light having the spectrum illustrated in FIG. 5 was used as a reference for comparison.

In each of the following Examples, the ratio of the intensity of fluorescence from the fluorescent agent to the intensity of background light was treated as a signal-to-noise ratio, and verification was performed.

Examples

Figure 15:
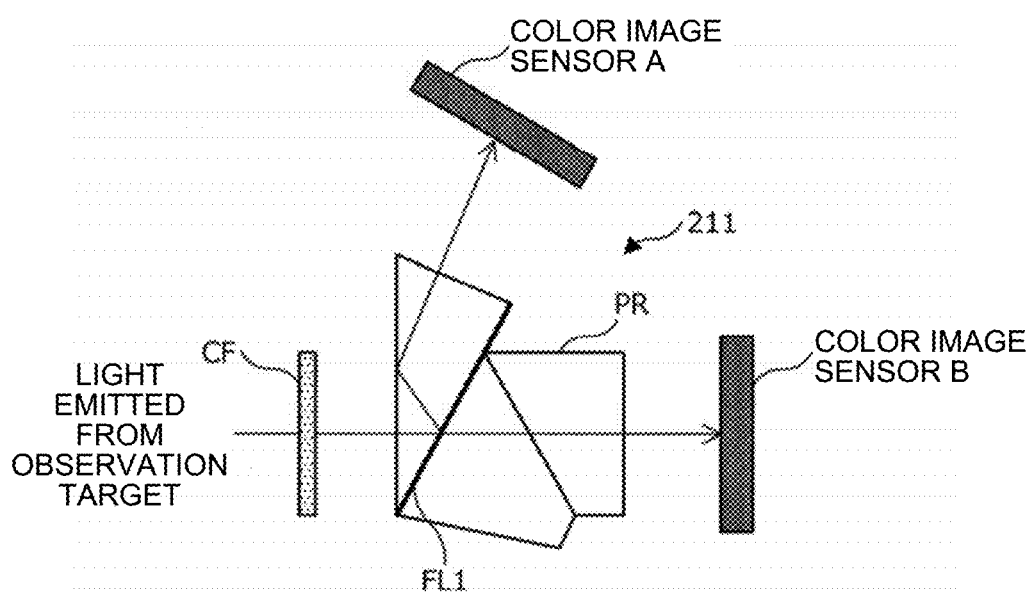
FIG. 15 is an explanatory diagram for describing an example.

It was assumed that the imaging optical system 211 provided in the imaging unit 20 is the imaging optical system as illustrated in FIG. 15, and a simulation was performed for a case of observing fluorescence from 5-ALA which is a fluorescent agent. Here, it was assumed that the wavelength selection filter FL1 has an optical characteristic of forming an image of the fluorescence of 5-ALA on a color image sensor B and forming an image of light in other wavelength bands on a color image sensor A.

Further, it is assumed that white light having a color temperature of 6000 K and color coordinates (X, Y)=(0.322, 0.341) is implemented by using the green light, blue light and white light described above.

As a result of the simulation, it was clarified that the signal-to-noise ratio related to the fluorescence of 5-ALA was improved by 2.3 times as compared with that in a case where only white light was used.

As described above, the preferred embodiments of the present disclosure have been described in detail with reference to the accompanying drawings, but the technical scope of the present disclosure is not limited to such examples. It will be apparent to those skilled in the art of the present disclosure that various modifications or alterations can be conceived within the scope of the technical idea described in the claims and it is naturally understood that these modifications or alterations fall within the technical scope of the present disclosure.

Furthermore, the effects described in the present specification are merely illustrative or exemplary and are not restrictive. That is, the technology according to the present disclosure can exhibit other effects obvious to those skilled in the art from the description of the present specification in addition to or in place of the above-described effects.

Note that the following configurations also fall within the technical scope of the present disclosure.

(1)
An image acquisition system comprising:
a first narrowband light source that emits first narrowband light for exciting a luminescent agent that exists in an observation target and emits light having a wavelength belonging to a visible light wavelength band;
a second narrowband light source that emits second narrowband light in a wavelength band of ±30 nm of a peak light emission wavelength of the luminescent agent;
a broadband light source that emits broadband light for illuminating the observation target, the broadband light being in a wavelength band broader than those of the first narrowband light and the second narrowband light;
a first image sensor on which an image of light in a light emission wavelength band including a wavelength corresponding to light emitted from the luminescent agent is formed; and
a second image sensor including one or more image sensors on which an image of light in a wavelength band other than the light emission wavelength band is formed,
wherein a first captured image obtained from the first image sensor and a second captured image obtained from the second image sensor are combined with each other to obtain a captured image related to the observation target.

(2)
The image acquisition system according to (1), wherein light having a predetermined color temperature and color coordinates is used as illumination light for illuminating the observation target, the light being obtained by at least multiplexing at least one of the first narrowband light or the second narrowband light, and the broadband light.

(3)
The image acquisition system according to (2), wherein in a case of not observing the light emitted from the luminescent agent, light having a predetermined color temperature and color coordinates is used as the illumination light, the light being implemented by multiplexing at least one of the first narrowband light or the second narrowband light, and the broadband light, and
in a case of observing the light emitted from the luminescent agent, light having a predetermined color temperature and color coordinates is used as the illumination light, the light being implemented by suppressing an intensity of the second narrowband light and increasing or decreasing intensities of the first narrowband light and the broadband light.

(4)
The image acquisition system according to (3), wherein in a case of observing the light emitted from the luminescent agent, the second narrowband light source is turned off or controlled so that a drive voltage is lower than an oscillation threshold voltage of the second narrowband light.

(5)
The image acquisition system according to (3) or (4), wherein in a case of not observing the light emitted from the luminescent agent, the first captured image and the second captured image are combined with each other to output a color captured image of the observation target, and
in a case of observing the light emitted from the luminescent agent, the first captured image and the second captured image are combined with each other to output a color captured image of the observation target, in which the light emitted from the luminescent agent is superimposed.

(6)
The image acquisition system according to any one of (2) to (5), wherein the illumination light is white light.

(7)
The image acquisition system according to any one of (2) to (6), wherein the narrowband light and the broadband light are multiplexed so that the color temperature is within a range of 5000 K or more and 6500 K or less, and the color coordinates (X, Y) are within a range in which X: 0.3 or more and 0.4 or less and Y: 0.3 or more and 0.4 or less.

(8)
The image acquisition system according to any one of (2) to (7), wherein the first narrowband light source, the second narrowband light source, and the broadband light source are driven independently of each other to control an intensity.

(9)
The image acquisition system according to any one of (1) to (8), further comprising a branching optical system that makes light from the observation target branch into light in the light emission wavelength band and light in a wavelength band other than the light emission wavelength band.

(10)
The image acquisition system according to (9), wherein the branching optical system includes: a wavelength selection filter that separates light in the light emission wavelength band and light in a wavelength band other than the light emission wavelength band from each other; and
at least one of a dichroic mirror or a color separation prism including a plurality of prisms.

(11)
The image acquisition system according to any one of (1) to (10), wherein an image of light from the observation target is formed on the first image sensor and the second image sensor via a medical microscope unit or a medical endoscope unit.

(12)
The image acquisition system according to any one of (1) to (11), wherein at least a blue narrowband light source that emits blue light, a green narrowband light source that emits green light, and a red narrowband light source that emits red light are included as narrowband light sources, and
at least one of the blue narrowband light source, the green narrowband light source, or the red narrowband light source functions as the first narrowband light source and/or the second narrowband light source.

(13)
The image acquisition system according to any one of (1) to (12), wherein as the first narrowband light source and the second narrowband light source, a laser light source, a semiconductor laser light source, or a light emitting diode is used independently of each other, and
as the broadband light source, a lamp light source, a light emitting diode, or a fluorescent material excitation light source is used.

(14)
The image acquisition system according to any one of (1) to (13), wherein the luminescent agent is at least one of fluorescein, 5-aminolevulinic acid (5-ALA), or Laserphyrin.

(15)
The image acquisition system according to any one of (1) to (14), wherein the observation target is a living tissue.

(16)
An image acquisition method comprising:
irradiating an observation target with illumination light from at least one of a first narrowband light source that emits first narrowband light for exciting a luminescent agent that exists in the observation target and emits light having a wavelength belonging to a visible light wavelength band or a second narrowband light source that emits second narrowband light in a wavelength band of ±30 nm of a peak light emission wavelength of the luminescent agent, and a broadband light source that emits broadband light for illuminating the observation target, the broadband light being in a wavelength band broader than those of the first narrowband light and the second narrowband light;

receiving, by each of a first image sensor on which an image of light in a light emission wavelength band including a wavelength corresponding to light emitted from the luminescent agent is formed and a second image sensor including one or more image sensors on which an image of light in a wavelength band other than the light emission wavelength band is formed, light from the observation target; and combining a first captured image obtained from the first image sensor and a second captured image obtained from the second image sensor with each other to obtain a captured image related to the observation target.

REFERENCE SIGNS LIST

1 IMAGE ACQUISITION SYSTEM
10 LIGHT SOURCE UNIT
20 IMAGING UNIT
30 ARITHMETIC PROCESSING UNIT
101 FIRST NARROWBAND LIGHT SOURCE
103 SECOND NARROWBAND LIGHT SOURCE
105 BROADBAND LIGHT SOURCE
111 NARROWBAND LIGHT SOURCE
113 MULTIPLEXING OPTICAL SYSTEM
115 ILLUMINATION OPTICAL SYSTEM
201 FIRST IMAGE SENSOR
203 SECOND IMAGE SENSOR
211 IMAGING OPTICAL SYSTEM
301 IMAGING PROCESSING CONTROL UNIT
303 DATA ACQUISITION UNIT
305 IMAGE PROCESSING UNIT
307 OUTPUT CONTROL UNIT
309 DISPLAY CONTROL UNIT
S OBSERVATION TARGET
LR LUMINESCENT AGENT

The invention claimed is:

1. An image acquisition system comprising:
a first narrowband light source that emits first narrowband light for exciting a luminescent agent that exists in an observation target and emits light having a wavelength belonging to a visible light wavelength band;
a second narrowband light source that emits second narrowband light in a wavelength band of ±30 nm of a peak light emission wavelength of the luminescent agent;
a broadband light source that emits broadband light for illuminating the observation target, the broadband light being in a wavelength band broader than those of the first narrowband light and the second narrowband light;
a first image sensor on which an image of light in a light emission wavelength band including a wavelength corresponding to light emitted from the luminescent agent is formed;
a second image sensor including one or more image sensors on which an image of light in a wavelength band other than the light emission wavelength band is formed, and
circuitry configured to:
receive selection of an observation mode, which is a first observation mode of performing normal observation using light in the visible light wavelength band or a second observation mode of performing observation using light emitted from the luminescent agent, from a user;
control the first narrowband light source, the second narrowband light source, and/or the broadband light source to irradiate the observation target on a basis of the observation mode;
control the first image sensor and the second image sensor to capture a first captured image and a second captured image, respectively; and
combine the first captured image obtained from the first image sensor and the second captured image obtained from the second image sensor to obtain a captured image related to the observation target.

2. The image acquisition system according to claim 1, wherein light having a predetermined color temperature and color coordinates is used as illumination light for illuminating the observation target, the illumination light being obtained by at least multiplexing at least one of the first narrowband light or the second narrowband light, and the broadband light.

3. The image acquisition system according to claim 2, wherein in a case of not observing the light emitted from the luminescent agent, light having a predetermined color temperature and color coordinates is used as the illumination light, the illumination light being implemented by multiplexing at least one of the first narrowband light or the second narrowband light, and the broadband light, and
in a case of observing the light emitted from the luminescent agent, light having a predetermined color temperature and color coordinates is used as the illumination light, the illumination light being implemented by suppressing an intensity of the second narrowband light and increasing or decreasing intensities of the first narrowband light and the broadband light.

4. The image acquisition system according to claim 3, wherein in a case of observing the light emitted from the luminescent agent, the second narrowband light source is turned off or controlled so that a drive voltage is lower than an oscillation threshold voltage of the second narrowband light.

5. The image acquisition system according to claim 3, wherein in a case of not observing the light emitted from the luminescent agent, the first captured image and the second captured image are combined with each other to output a color captured image of the observation target, and
in a case of observing the light emitted from the luminescent agent, the first captured image and the second captured image are combined with each other to output a color captured image of the observation target, in which the light emitted from the luminescent agent is superimposed.

6. The image acquisition system according to claim 2, wherein the illumination light is white light.

7. The image acquisition system according to claim 2, wherein the narrowband light and the broadband light are multiplexed so that the color temperature is within a range of 5000 K or more and 6500 K or less, and the color coordinates (X, Y) are within a range in which X: 0.3 or more and 0.4 or less and Y: 0.3 or more and 0.4 or less.

8. The image acquisition system according to claim 2, wherein the first narrowband light source, the second narrowband light source, and the broadband light source are driven independently of each other to control an intensity.

9. The image acquisition system according to claim 1, further comprising a branching optical system that makes light from the observation target branch into light in the light emission wavelength band and light in a wavelength band other than the light emission wavelength band.

10. The image acquisition system according to claim 9, wherein the branching optical system includes: a wavelength selection filter that separates light in the light emission wavelength band and light in a wavelength band other than the light emission wavelength band from each other; and
 at least one of a dichroic mirror or a color separation prism including a plurality of prisms.

11. The image acquisition system according to claim 1, wherein an image of light from the observation target is formed on the first image sensor and the second image sensor via a medical microscope unit or a medical endoscope unit.

12. The image acquisition system according to claim 1, wherein at least a blue narrowband light source that emits blue light, a green narrowband light source that emits green light, and a red narrowband light source that emits red light are included as narrowband light sources, and
 at least one of the blue narrow/band light source, the green narrowband light source, or the red narrowband light source functions as the first narrowband light source and/or the second narrowband light source.

13. The image acquisition system according to claim 1, wherein as the first narrowband light source and the second narrowband light source, a laser light source, a semiconductor laser light source, or a light emitting diode is used independently of each other, and
 as the broadband light source, a lamp light source, a light emitting diode, or a fluorescent material excitation light source is used.

14. The image acquisition system according to claim 1, wherein the luminescent agent is at least one of fluorescein, 5-aminolevulinic acid (5-ALA), or Laserphyrin.

15. The image acquisition system according to claim 1, wherein the observation target is a living tissue.

16. An image acquisition method comprising:
receiving selection of an observation mode, which is a first observation mode of performing normal observation using light in the visible light wavelength band or a second observation mode of performing observation using light emitted from the luminescent agent, from a user;
irradiating an observation target with illumination light from at least one of a first narrowband light source that emits first narrowband light for exciting a luminescent agent that exists in the observation target and emits light having a wavelength belonging to a visible light wavelength band or a second narrowband light source that emits second narrowband light in a wavelength band of ±30 nm of a peak light emission wavelength of the luminescent agent, and a broadband light source that emits broadband light for illuminating the observation target, the broadband light being in a wavelength band broader than those of the first narrowband light and the second narrowband light on a basis of the observation mode;
receiving, by each of a first image sensor on which an image of light in a light emission wavelength band including a wavelength corresponding to light emitted from the luminescent agent is formed and a second image sensor including one or more image sensors on which an image of light in a wavelength band other than the light emission wavelength band is formed, light from the observation target; and
combining a first captured image obtained from the first image sensor and a second captured image obtained from the second image sensor with each other to obtain a captured image related to the observation target.

* * * * *